US010912283B2

(12) United States Patent
Vrabete et al.

(10) Patent No.: US 10,912,283 B2
(45) Date of Patent: Feb. 9, 2021

(54) TECHNOLOGIES FOR MANAGING THE HEALTH OF LIVESTOCK

(71) Applicant: Intel Corporation, Santa Clara, CA (US)

(72) Inventors: Bradut Vrabete, Sixmilebridge (IE); Mark Kelly, Leixlip (IE); Keith Nolan, Mullingar (IE)

(73) Assignee: Intel Corporation, Santa Clara, CA (US)

( * ) Notice: Subject to any disclaimer, the term of this patent is extended or adjusted under 35 U.S.C. 154(b) by 328 days.

(21) Appl. No.: 15/089,477

(22) Filed: Apr. 2, 2016

(65) Prior Publication Data

US 2017/0280687 A1    Oct. 5, 2017

(51) Int. Cl.
*A01K 29/00* (2006.01)
*A01K 11/00* (2006.01)
(Continued)

(52) U.S. Cl.
CPC .......... *A01K 29/005* (2013.01); *A01K 11/004* (2013.01); *A01K 11/006* (2013.01); *G06Q 50/02* (2013.01); *G16H 40/63* (2018.01)

(58) Field of Classification Search
CPC .............. G06F 19/322; G06Q 10/0833; G06Q 10/087; G06Q 50/02; G06Q 50/24;
(Continued)

(56) References Cited

U.S. PATENT DOCUMENTS 4,470,212 A  *  9/1984  Stafford ............... A01K 11/001
                                                         40/300
4,617,876 A  *  10/1986  Hayes ................. A01K 1/0023
                                                         119/51.02
(Continued)

FOREIGN PATENT DOCUMENTS

WO      2013/082227      6/2013
WO      2016/037190      3/2016

OTHER PUBLICATIONS

European Office action for European application No. 17159248.8 dated Aug. 12, 2019 (7 pages).
(Continued)

*Primary Examiner* — Fekadeselassie Girma
(74) *Attorney, Agent, or Firm* — Hanley, Flight and Zimmerman, LLC

(57) ABSTRACT

Technologies for managing the health of livestock include one or more livestock health sensor systems configured to determine livestock health data of livestock animals. The livestock health data includes livestock health characteristic data indicative of a health characteristic of the corresponding livestock animal associated livestock identification data that uniquely identifies each livestock animal. The livestock identification data is received by each livestock health sensor system from a livestock identification tag coupled to the corresponding livestock animal. Each livestock health sensor system transmits the determined livestock health data to a livestock health monitoring server, which aggregates the livestock health data for each livestock animal and analyzes
(Continued)

the health data to determine whether any abnormalities are present. If so, the livestock health monitoring server may control a livestock treatment device to provide treatment to the corresponding livestock animal on a per-animal basis.

22 Claims, 14 Drawing Sheets

(51) Int. Cl.
*G06Q 50/02* (2012.01)
*G16H 40/63* (2018.01)

(58) Field of Classification Search
CPC ............ G07C 9/00111; G08B 13/2408; G08B 13/2417; G08B 13/2431; G08B 13/2437; G08B 13/2471; G08B 13/2474; G08B 23/00
See application file for complete search history.

(56) References Cited

U.S. PATENT DOCUMENTS

| | | | | |
|---|---|---|---|---|
| 4,655,170 A * | 4/1987 | DaSilva | | A01K 11/006 119/51.02 |
| 4,663,625 A * | 5/1987 | Yewen | | G08B 13/2408 340/10.42 |
| 5,320,067 A * | 6/1994 | Legrain | | A01K 1/0613 119/51.02 |
| 6,613,179 B1 * | 9/2003 | McCoy | | B32B 38/14 156/277 |
| 7,170,413 B1 * | 1/2007 | Waterhouse | | A01K 11/004 340/572.1 |
| 7,228,816 B2 * | 6/2007 | Turner | | A01K 5/0114 119/51.02 |
| 7,874,265 B1 * | 1/2011 | Addleman | | A01K 5/025 119/63 |
| 9,084,411 B1 * | 7/2015 | McGlone | | A01K 29/00 |
| 10,085,419 B2 * | 10/2018 | Zimmerman | | G06K 7/10366 |
| 2001/0032594 A1 * | 10/2001 | Bickley | | A01K 5/0114 119/55 |
| 2003/0229452 A1 * | 12/2003 | Lewis | | G06Q 50/24 702/19 |
| 2004/0077713 A1 * | 4/2004 | Maupin | | C07C 49/583 514/475 |
| 2005/0009122 A1 * | 1/2005 | Whelan | | G16H 10/40 435/7.32 |
| 2005/0086132 A1 * | 4/2005 | Kanitz | | G06Q 10/08 705/28 |
| 2005/0145187 A1 * | 7/2005 | Gray | | A01K 29/00 119/174 |
| 2006/0011144 A1 * | 1/2006 | Kates | | G01S 13/86 119/719 |
| 2006/0011145 A1 * | 1/2006 | Kates | | A01K 15/02 119/719 |
| 2006/0178579 A1 * | 8/2006 | Haynes | | G01G 13/24 600/437 |
| 2006/0249088 A1 * | 11/2006 | Eu | | A01K 27/009 119/51.02 |
| 2008/0068136 A1 * | 3/2008 | Malik | | H04W 8/245 340/10.5 |
| 2008/0252426 A1 * | 10/2008 | Lee | | G06K 19/0701 340/10.3 |
| 2009/0135020 A1 * | 5/2009 | Hsiao | | G08B 5/36 340/686.1 |
| 2009/0145364 A1 * | 6/2009 | Hardy | | A01K 1/0613 119/14.04 |
| 2010/0030036 A1 * | 2/2010 | Mottram | | A61B 5/4519 600/301 |
| 2010/0089329 A1 * | 4/2010 | Lefferson | | A01K 1/0209 119/51.02 |
| 2010/0123583 A1 * | 5/2010 | Bommer | | G08B 21/20 340/572.7 |
| 2010/0132629 A1 * | 6/2010 | Jalbert | | A01K 5/0121 119/720 |
| 2010/0277286 A1 * | 11/2010 | Burkart | | G06K 19/0701 340/10.34 |
| 2010/0289643 A1 * | 11/2010 | Trundle | | H04L 12/282 340/545.1 |
| 2010/0289644 A1 * | 11/2010 | Slavin | | G08B 21/18 340/568.1 |
| 2011/0022851 A1 * | 1/2011 | Yokota | | H04L 9/0894 713/189 |
| 2011/0169657 A1 * | 7/2011 | August | | A01K 11/004 340/854.6 |
| 2012/0294876 A1 * | 11/2012 | Zimmerman | | A61P 37/04 424/184.1 |
| 2012/0313785 A1 * | 12/2012 | Hanson | | G08B 23/00 340/573.1 |
| 2012/0326874 A1 * | 12/2012 | Kwak | | A01K 11/006 340/573.3 |
| 2013/0222141 A1 * | 8/2013 | Rhee | | G16H 50/80 340/573.3 |
| 2014/0097940 A1 * | 4/2014 | Kwak | | G06K 19/0723 340/10.1 |
| 2014/0275824 A1 * | 9/2014 | Couse | | G16H 40/60 600/301 |
| 2014/0347184 A1 | 11/2014 | Triener | | |
| 2014/0350410 A1 * | 11/2014 | Axelsson | | A61B 5/0077 600/476 |
| 2015/0282457 A1 * | 10/2015 | Yarden | | A61D 17/00 340/573.2 |
| 2015/0318624 A1 * | 11/2015 | Schantz | | G01S 5/14 343/867 |
| 2015/0342150 A1 * | 12/2015 | Womble | | G06K 9/00362 119/718 |
| 2015/0371458 A1 * | 12/2015 | Scott | | G07C 5/085 701/29.1 |
| 2016/0037755 A1 * | 2/2016 | Webster | | A61B 5/7282 600/304 |
| 2016/0120154 A1 * | 5/2016 | Hill | | A01K 11/008 340/573.3 |
| 2016/0129913 A1 * | 5/2016 | Boesen | | B60W 40/09 705/4 |
| 2016/0135426 A1 * | 5/2016 | Harty | | A61B 5/7282 340/573.3 |
| 2016/0174099 A1 * | 6/2016 | Goldfain | | H04W 28/0226 375/130 |
| 2016/0178392 A1 * | 6/2016 | Goldfain | | G06F 19/3418 702/104 |
| 2016/0227738 A1 * | 8/2016 | Ausman | | A01K 5/025 |
| 2016/0352887 A1 * | 12/2016 | Na | | H04M 1/72527 |
| 2017/0006838 A1 * | 1/2017 | Brayer | | A01K 15/029 |
| 2017/0124264 A1 * | 5/2017 | Jordan | | G16H 40/20 |
| 2017/0143249 A1 * | 5/2017 | Davis | | A61B 5/1032 |
| 2017/0159122 A1 * | 6/2017 | Zhang | | C12Q 1/6883 |
| 2017/0174221 A1 * | 6/2017 | Vaughn | | G05D 1/021 |
| 2017/0223926 A1 * | 8/2017 | Ausman | | A01K 11/006 |
| 2017/0280687 A1 * | 10/2017 | Vrabete | | G16H 40/63 |
| 2017/0334354 A1 * | 11/2017 | Hatton | | B60Q 9/008 |
| 2018/0027371 A1 * | 1/2018 | Austraat | | H04M 1/72572 455/456.3 |
| 2018/0206455 A1 * | 7/2018 | Thiex | | A01K 11/004 |
| 2018/0208209 A1 * | 7/2018 | Al-Dahle | | B60W 10/22 |
| 2018/0374165 A1 * | 12/2018 | Ferro dos Santos | | G06Q 10/00 |
| 2019/0016343 A1 * | 1/2019 | Allen | | G08G 1/202 |
| 2019/0019122 A1 * | 1/2019 | Allen | | G06Q 50/30 |
| 2019/0019133 A1 * | 1/2019 | Allen | | G06Q 10/02 |
| 2019/0050787 A1 * | 2/2019 | Munafo | | G06Q 10/06311 |
| 2019/0098869 A1 * | 4/2019 | Forster | | A01K 11/004 |
| 2019/0288868 A1 * | 9/2019 | Mosalem | | H04L 12/2829 |
| 2020/0178505 A1 * | 6/2020 | Womble | | A01M 29/00 |

OTHER PUBLICATIONS

Extended European search report for European application dated Aug. 31, 2017 (9 pages).

(56) References Cited

OTHER PUBLICATIONS

European Office action for European application No. 17159248.8 dated May 25, 2020 (5 pages).

* cited by examiner

TECHNOLOGIES FOR MANAGING THE HEALTH OF LIVESTOCK

BACKGROUND

Present day livestock health management techniques typically apply a per-herd treatment philosophy to treat various ailments affecting the herd. Even in those cases in which an outbreak of a disease, such as liver fluke, is identified in only one or a few livestock animals of the herd, the entire herd to which the identified livestock animals belong is often treated. While such treatment plans ensure coverage of possibly infected livestock that have not yet outwardly shown symptoms of the disease, per-herd treatment also treats healthy livestock animals of the herd resulting in overtreatment for those healthy livestock animals. Such overtreatment can result in the development of resistant strains of diseases and an increase the overall cost of livestock health maintenance.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements.

DETAILED DESCRIPTION OF THE DRAWINGS

Figure 1:
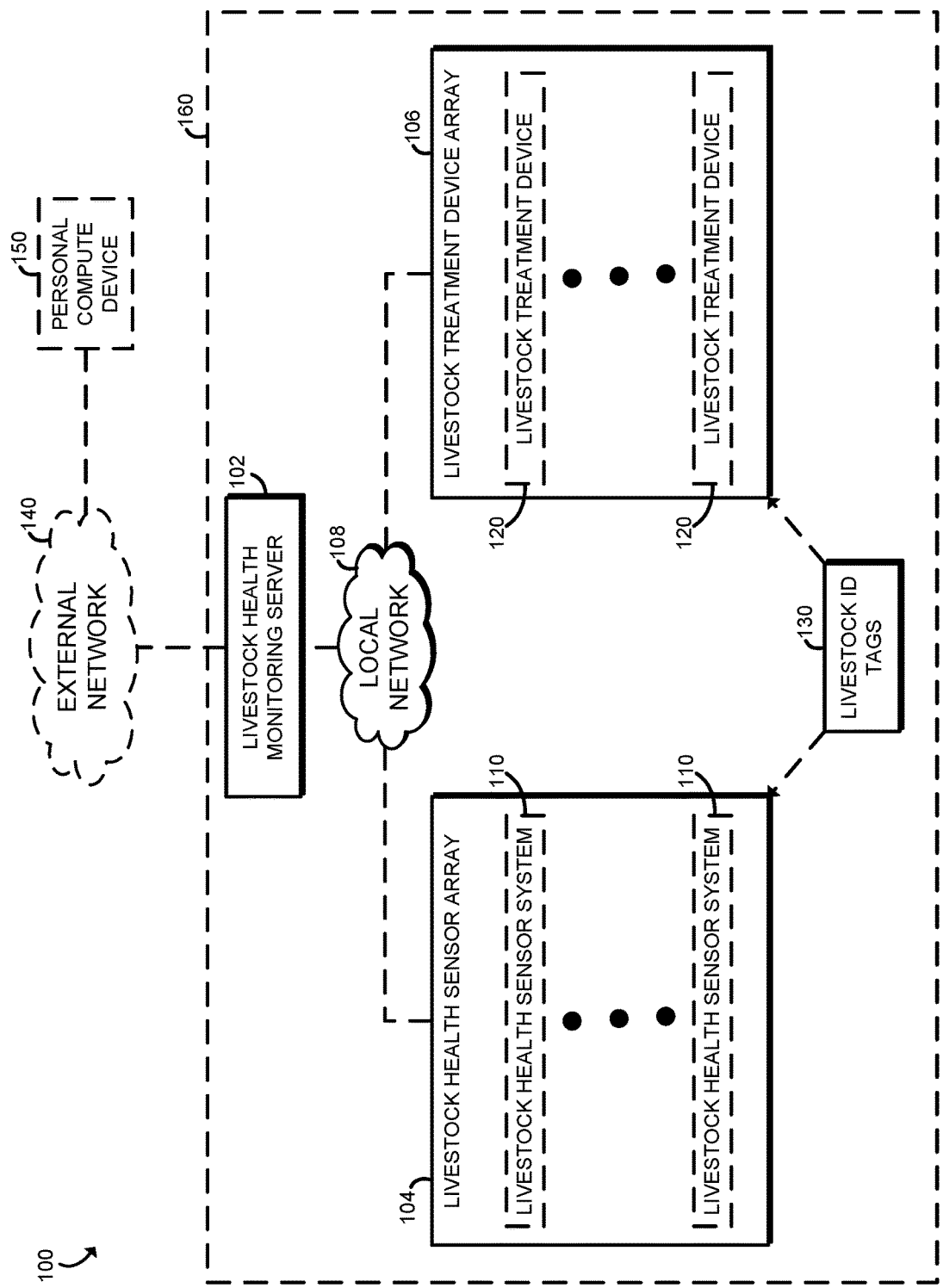
FIG. 1 is a simplified block diagram of at least one embodiment of a system for managing the health of livestock.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, an illustrative system 100 for managing the health of livestock animals includes a livestock health monitoring server 102 in communication with a livestock health sensor array 104 and a livestock treatment device array 106 over a local network 108. The livestock health sensor array 104 includes one or more livestock health sensor systems 110, each of which is configured to determine livestock health data of monitored livestock animals. Similarly, the livestock treatment device array 106 includes one or more livestock treatment devices 120, each of which is configured to provide a treatment to one or more livestock animals on a per-animal basis as discussed in more detail below. To better monitor the health of each livestock animal and ensure the per-animal treatment, the system 100 also includes a livestock identification tag 130 attached, implanted, or otherwise coupled to each monitored livestock animal. As discussed in more detail below, each livestock identification tag includes livestock identification data that uniquely identifies the livestock animal to which it is coupled.

In use, as discussed in more detail below, a livestock health sensor system 110 receives the livestock identification data of a livestock animal from the livestock identification tag coupled to the livestock animal when the livestock animal is in the presence (e.g., nearby) of the livestock health sensor system 110. The livestock health sensor system 110 also determines livestock health characteristic data indicative of a health characteristic (e.g., feeding proclivity, temperature, mobility, weight, disease presence, etc.) of the livestock animal. The livestock health sensor system 110 transmits the health data, which includes the livestock health characteristic data associated with the livestock identification data, to the livestock health monitoring server 102.

The livestock health monitoring server 102 performs various analyses on the livestock health characteristic data to determine whether any data is abnormal. For example, in some embodiments, the livestock health monitoring server 102 may aggregate the health characteristic data with historical livestock health characteristic data of the livestock animal to determine a historical trend to the livestock health characteristic data or a set of livestock health characteristic data of the livestock animal. Such historical trend may date back to the birth of the livestock animal in some embodiments (i.e., the system 100 may monitor the health of livestock animals over the course of the life of the livestock animal).

If the livestock health monitoring server 102 determines that an abnormality is present in the health data of one or more livestock animals, the livestock health monitoring server 102 transmits an alert notification to other components of the system 100. For example, the livestock health monitoring server 102 may transmit the alert notification to a livestock health sensor system(s) 110, a livestock treatment device(s) 120, the livestock identification tag 130 of the relevant livestock animal, and/or a personal compute device 150 of a user of the system 100 (e.g., a farm owner) over an external network 140. The alert notification may include the livestock health characteristic data considered to be abnormal and/or the livestock identification data of the associated livestock animals. In the illustrative embodiment, for example, the livestock health monitoring server 102 transmits an alert notification to one or more livestock treatment devices 120 to control treatment (e.g., quarantine or dispensing of a medicine) of the livestock animals in question. The alert notification may include the livestock identification data of the livestock animal(s) to be treated and an instruction to control the activation of the livestock treatment device based on the livestock identification data as discussed in more detail below.

Figure 2:
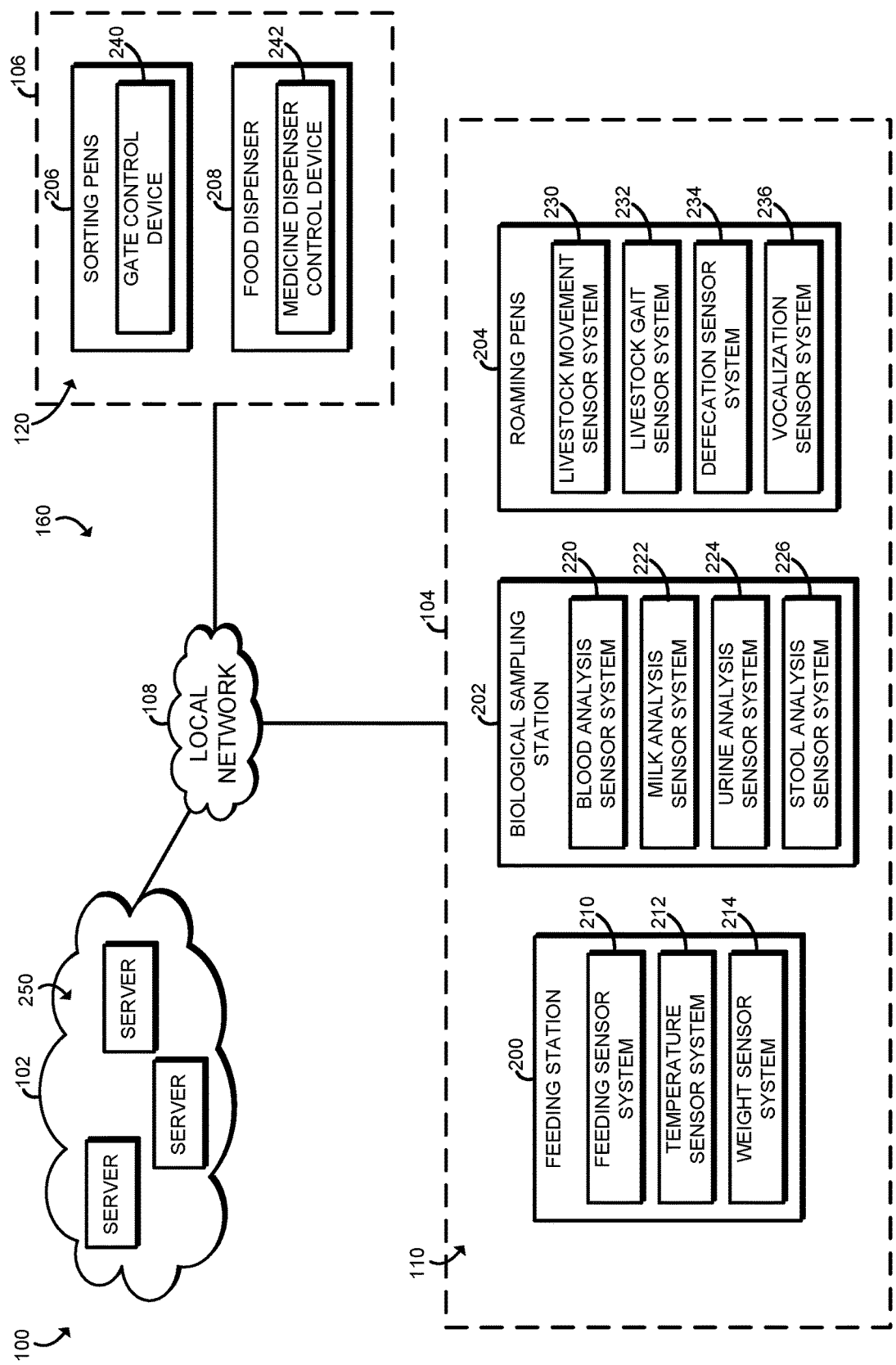
FIG. 2 is a simplified block diagram of another embodiment of the system of FIG. 1.

Each of the livestock health sensor systems 110 and the livestock treatment devices 120 may be arranged or installed throughout an animal farm, business, or other location 160 capable of housing and/or maintaining livestock animals, which may be embodied as any type of animal whose health can be monitored (e.g., cattle, pigs, racing horses, chicken, etc.). An illustrative embodiment of a farm or location 160 having the system 100 installed therein is shown in FIG. 2. As shown, the illustrative system 100 includes a number of livestock health sensor systems 110 installed or coupled to various stations, structures, or locations of the farm 160. For example, the system 100 of FIG. 2 includes a feeding sensor system 210, a temperature sensor system 212, and a weight sensor system 214 coupled to or forming a part of a feeding station 200. In use, the feeding sensor system 210 may be configured to determine livestock health characteristic data indicative of a feeding pattern or proclivity of livestock animals consuming food from the feeding station 200. Similarly, the temperature sensor system 212 may be configured to determine livestock health characteristic data indicative of a temperature of livestock animals consuming food from the feeding station 200. Additionally, the weight sensor system 214 may be configured to determine livestock health characteristic data indicative of a weight of livestock animals consuming food from the feeding station 200.

The system 100 of FIG. 2 also includes a blood analysis sensor system 220, a milk analysis sensor system 222, a urine analysis sensor system 224, and a stool analysis sensor system 226 coupled to or forming a part of a biological sampling station 202. In use, the blood analysis sensor system 220 may be configured to determine livestock health characteristic data indicative of various aspects or characteristics (e.g., presence or absence of a monitored disease) of the blood of the livestock animal based on a blood sample obtained at the biological sampling station 202. Similarly, the milk analysis sensor system 222 may be configured to determine livestock health characteristic data indicative of various aspects or characteristics (e.g., presence or absence of a monitored disease) of the milk of the livestock animal based on a milk sample obtained at the biological sampling station 202. Additionally, the urine analysis sensor system 224 may be configured to determine livestock health characteristic data indicative of various aspects or characteristics (e.g., presence or absence of a monitored disease) of the urine of the livestock animal based on a urine sample obtained at the biological sampling station 202. The stool analysis sensor system 226 may be configured to determine livestock health characteristic data indicative of various aspects or characteristics (e.g., presence or absence of a monitored disease) of the stool of the livestock animal based on a stool sample obtained at the biological sampling station 202.

Additionally, the system 100 of FIG. 2 also includes a livestock movement sensor system 230, a livestock gait sensor system 232, a defecation sensor system 234, and a vocalization sensor system 236 coupled to or forming a part of one or more roaming pens 204. In use, the livestock movement sensor system 230 may be configured to determine livestock health characteristic data indicative of the movement or mobility of livestock animals roaming in the roaming pen 204. Similarly, the livestock gait sensor system 232 may be configured to determine livestock health characteristic data indicative of a gait or motion of livestock animals roaming in the roaming pen 204. The defecation sensor system 234 may be configured to determine livestock health characteristic data indicative of the regularity of defecation of livestock animals roaming in the roaming pen 204. Additionally, the vocalization sensor system 236 may be configured to determine livestock health characteristic data indicative of vocalizations or noises made by the livestock animals roaming in the roaming pen 204.

As shown in FIG. 2, the illustrative system 100 also includes a number of livestock treatment device 120 installed or coupled to various stations, structures, or locations of the farm 160. For example, the system 100 of FIG. 2 includes a gate control device 240 coupled to or forming part of a sorting pen 206. In use, the gate control device 240 is configured to control actuation of the a gate of the sorting pen based on the livestock identification data received from the livestock health monitoring server 102 to separate or quarantine livestock animals. The illustrative system 100 also includes a medicine dispenser control device 242 coupled to or forming a part of a food dispenser 208. In use, the medicine dispenser control device 242 is configured to control actuation of a medicine dispenser to provide medicine to a livestock animal (e.g., in the food of the livestock animal).

Of course, it should be understood that the livestock health sensor systems 110 and the livestock treatment devices 120 of the system 100 of FIG. 2 are merely illustrative. In other embodiments, the system 100 may include additional or other livestock health sensor systems 110 and the livestock treatment devices 120 configured to sense other types of livestock health characteristic data and provide other types of treatment to livestock animals. Additionally, as discussed above, each of the livestock health sensor systems 110 and the livestock treatment devices 120 of the system 100 of FIG. 2 is configured to perform their various functions based on the livestock identification data associated with each livestock animal such that the sensing of livestock health characteristic data and the providing of treatment is done on a per-animal basis rather than a per-herd basis. As such, as discussed in more detail below, each livestock health sensor system 110 and livestock treatment device 120 includes circuitry and components to detect or receive the livestock identification data from the livestock identification tag 130 coupled to each livestock animal and perform their corresponding function based on the received livestock identification data (e.g., to treat the appropriate livestock animal).

As discussed above, each livestock health sensor system 110 and livestock treatment device 120 may communicate are configured to communicate with the livestock health monitoring sever 102 over the local network 108. The livestock health monitoring server 102 is configured to monitor, manage, and responds to health data indicative of the health of the livestock animals as discussed in more detail below. Although the livestock health monitoring server 102 is shown as a single compute device in FIG. 1, the livestock health monitoring server 102 may be embodied as a distributed or cloud-based server as shown in FIG. 2 in some embodiments. In such embodiments, the functionality of the livestock health monitoring server 102, which is described in more detail below, may be distributed across multiple servers 150. Alternatively, in yet other embodiments, the functionality of the livestock health monitoring server 102 may be distributed between local and remote servers.

Figure 3:
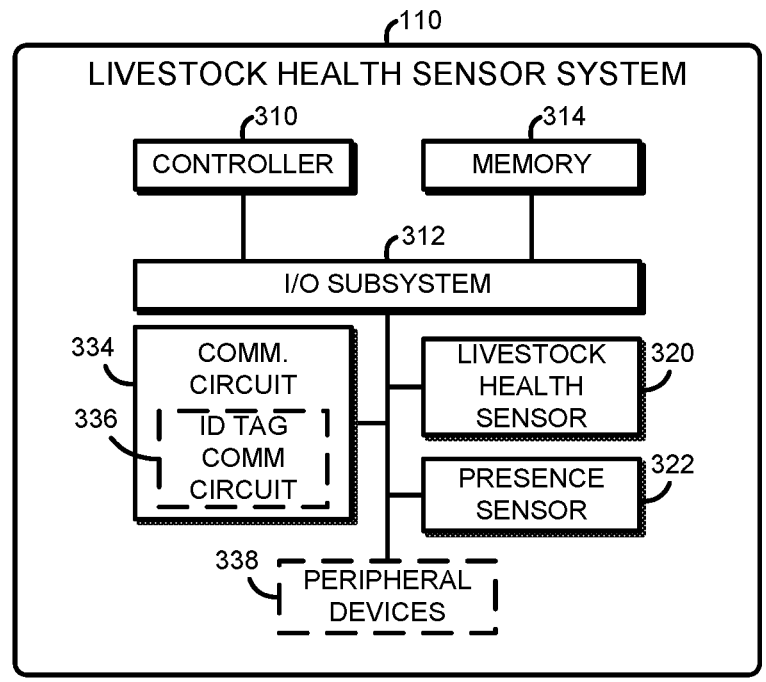
FIG. 3 is a simplified block diagram of at least one embodiment of a livestock health sensor system of the system of FIG. 1.

Referring now to FIG. 3, each livestock health sensor system 110 may be embodied as any type of sensing system or compute device capable of sensing or determining a health characteristic of a livestock animal. As discussed above, the health characteristic sensed or monitored by each livestock health sensor system 110 may be embodied as any type of characteristic or aspect of the health of a livestock animal such as its weight, temperature, blood pressure, feeding habits, defecating habits, movement, gait motion, biological sample health, and/or other health characteristic. The illustrative livestock health sensor system 110 is embodied as a "smart" sensor configured to sense the livestock health characteristic data and perform other related functions. However, in other embodiments, one or more of the livestock health sensor systems 110 of the system 100 may be embodied as "dumb" sensors having few components and configured to simply sense and report the corresponding livestock health characteristic data.

As shown in FIG. 3, each livestock health sensor system 110 illustratively includes a controller 310, a memory 314, an I/O subsystem 312, a livestock health sensor 320, a presence sensor 322, and a communication circuit 334. Of course, the livestock health sensor system 110 may include other or additional components, such as those commonly found in a sensor or sensing system, in other embodiments. Additionally, in some embodiments, one or more of the illustrative components may be incorporated in, or otherwise form a portion of, another component. For example, the memory 314, or portions thereof, may be incorporated in the controller 310 in some embodiments.

The controller 310 may be embodied as any type of controller or processor capable of performing the functions described herein. The controller 310 may be embodied as a microcontroller, single or multi-core processor(s), digital signal processor, or other controller, processor, or processing/controlling circuit. Similarly, the memory 314 may be embodied as any type of volatile or non-volatile memory or data storage capable of performing the functions described herein. In operation, the memory 314 may store various data and software used during operation of the livestock health sensor system 110. The memory 314 is communicatively coupled to the controller 310 via the I/O subsystem 312, which may be embodied as circuitry and/or components to facilitate input/output operations with the controller 310, the memory 314, and other components of the livestock health sensor system 110. For example, the I/O subsystem 312 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 312 may form a portion of a system-on-a-chip (SoC) and be incorporated, along with the controller 310, the memory 314, and other components of the livestock health sensor system 110, on a single integrated circuit chip.

The livestock health sensor 320 may be embodied as any type of sensor, sensing elements, or collection of sensors/sensing elements capable of producing sensor data indicative of a health characteristic of a livestock animal. For example, the livestock health sensor 320 may be embodied as a temperature sensor, a weight sensor, a camera, a sensor-on-a-chip, a microphone, or other sensor or sensing element. In this way, the livestock health sensor 320 may be a complex sensor (e.g., a sensor-on-a-chip) or a simple sensor (a weight sensor) depending on the particular health characteristic the livestock health sensor 320 is configured to sense. Although show in FIG. 3 as having a single livestock health sensor 320, it should be appreciated that each livestock health sensor system 110 may have one or more livestock health sensors 320, each of which may monitor or sense the same or different health characteristic of a livestock animal.

The presence sensor 322 may be embodied as any type of sensor or sensing circuit capable of producing sensor data indicative of a presence of a livestock animal in the vicinity of the corresponding livestock health sensor system 110. For example, in some embodiments, the presence sensor 322 may be embodied as an infra-red sensor, a weight sensor, a camera, a motion detector, a communication circuit, or other sensor or sensing circuit capable of detecting the presence of a livestock animal. In some embodiments, the presence sensor 322 may sense or detect the presence of a livestock animal based on transmissions (e.g., broadcasts) received from a livestock identification tag 130 attached to the corresponding livestock animal.

The communication circuit 334 of the livestock health sensor system 110 may be embodied as any communication circuit, device, or collection thereof, capable of enabling communications between the livestock health sensor system 110 and other components of the system 100 such as the livestock health monitoring server 102 and/or the livestock identification tags 130. The communication circuitry 334 may be configured to use any one or more communication technology (e.g., wired or wireless communications) and associated protocols (e.g., Ethernet, Bluetooth®, Wi-Fi®, WiMAX, WPAN, LoRaWAN, etc.) to effect such communication. In some embodiments, the communication circuitry 334 may include any number of other radio communications equipment, such as transceivers compatible with the Bluetooth® standard as defined by the Bluetooth® special interest group. For example, the communication circuit 334 may communicate over a wireless personal area network (WPAN) according to the IEEE 802.15.4 and IEEE 802.15.4g standards, among others. Additionally or alternatively, the communication circuit 334 may communicate over a wide area using LoRaWAN (Long Range Wide Area Network) developed by Semtech and the LoRa Alliance, Sigfox, and other ultra-narrow band technologies. As discussed in more detail below in regard to FIG. 19, those technologies may be used to establish a mesh network between the example communication circuit 334 and other devices, as well as external networks.

In some embodiments, the communication circuit 334 may include an identification tag communication circuit 336 configured to transmit or broadcast an interrogation signal to the livestock identification tags 130 to cause the livestock identification tags 130 to transmit their respective livestock identification data. For example, in some embodiments, the identification tag communication circuit 336 may be embodied as or otherwise include a radio-frequency identification (RFID) transmission circuit.

In some embodiments, the livestock health sensor system 110 may also include one or more other peripheral devices 338. Such peripheral devices 338 may be embodied as any type of device or component commonly found in a sensor system such as output devices or input devices.

Figure 4:
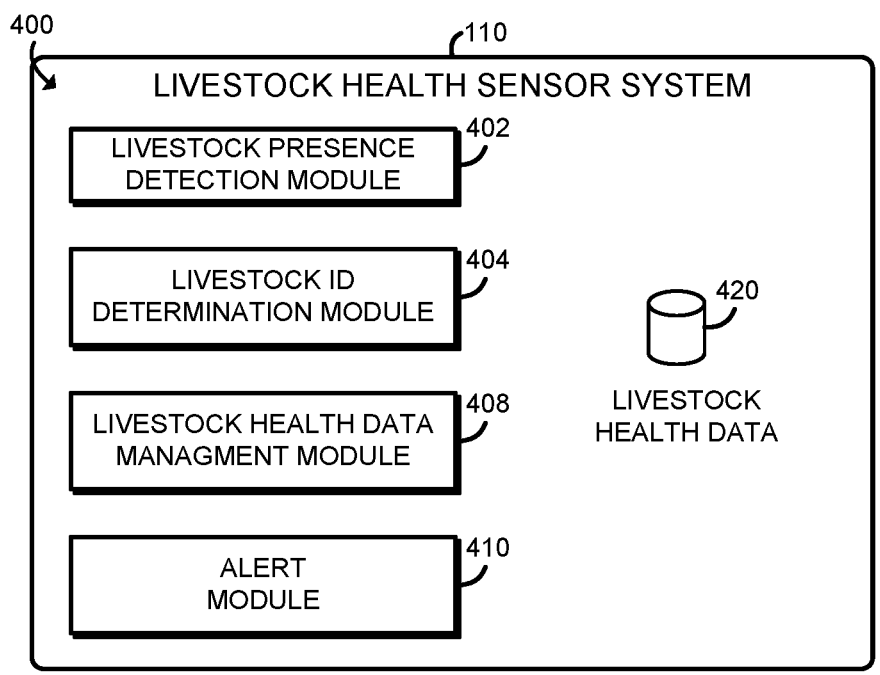
FIG. 4 is a simplified block diagram of at least one embodiment of an environment that may be established by the livestock health sensor system of FIG. 3.

Referring now to FIG. 4, in use, each livestock health sensor system 110 may establish an environment 400. The illustrative environment 400 includes a livestock presence detection module 402, a livestock identification determination module 404, and a livestock health data management module 408, and an alert module 410. Each of the modules, logic, and other components of the environment 400 may be embodied as hardware, firmware, software, or a combination thereof. As such, in some embodiments, one or more of the modules of the environment 400 may be embodied as circuitry or collection of electrical devices (e.g., a livestock presence detection circuit 402, a livestock identification determination circuit 404, and a livestock health data management circuit 408, an alert circuit 410, etc.). It should be appreciated that, in such embodiments, one or more of the livestock presence detection circuit 402, a livestock identification determination circuit 404, and a livestock health data management circuit 408, and/or an alert circuit 410 may form a portion of one or more of the controller 310, the memory 314, the I/O subsystem 312, the livestock health sensor 320, the presence sensor 322, the communication circuit 334, and/or other components of the livestock health sensor system 110. Additionally, in some embodiments, one or more of the illustrative modules may form a portion of another module and/or one or more of the illustrative modules may be independent of one another. Further, in some embodiments, one or more of the modules of the environment 400 may be embodied as virtualized hardware components or emulated architecture, which may be established and maintained by the controller 310 or other components of the livestock health sensor system 110.

The livestock presence detection module 402 is configured to determine whether a livestock animal is present in the vicinity of the livestock health sensor system 110. To do so, the livestock presence detection module 402 may monitor the sensor data produce d by the presence sensor 322 and determine the presence (or lack thereof) of a livestock animal based on such sensor data. As discussed above, in some embodiments, the livestock presence detection module 402 may determine the presence of a livestock animal based on transmission received from a livestock identification tag 130 coupled to the livestock animal.

The livestock identification determination module 404 is configured to determine the identity of a livestock animal that has been detected within the vicinity of the livestock health sensor system 110 by the livestock presence detection module 402. To do so, the livestock identification determination module 404 receives livestock identification data from the livestock identification tag 130 coupled to the detected livestock animal. In some embodiments, the livestock identification determination module 404 may transmit, via the identification tag communication circuit 336, an interrogation signal to the livestock identification tag 130 to cause the livestock identification tag 130 to transmit its corresponding livestock identification data.

The livestock health data management module 408 is configured to determine health data 420 of the detected livestock animal based on the sensor data produced by the livestock health sensor 320. To do so, the livestock health data management module 408 may determine livestock health characteristic data indicative of a health characteristic of the livestock animal and associate the livestock health characteristic data with the livestock identification data of that livestock animal. The livestock health data management module 408 may store the determined livestock health data locally and/or transmit the livestock health data to the livestock health monitoring server 102. For example, in some embodiments, the livestock health data management module 408 may determine and store livestock health data for a period of time and periodically transmit the livestock health data to the livestock health monitoring server 102.

In some embodiments, the livestock health data management module 408 may also be configured to locally analyze the livestock health data. For example, the livestock health data management module 408 may compare the determine livestock health characteristic data to thresholds or ranges to determine whether the determine livestock health characteristic data is abnormal or otherwise outside of an expected range or value. If the livestock health data management module 408 determines that the livestock health characteristic data is abnormal, the alert module 410 generates an alert notification, which the alert module may transmit to the livestock health monitoring server 102 and/or the livestock identification tag 130 of the respective livestock animal. The alert notification may include the determined livestock health characteristic data and the associated livestock identification data. In embodiments in which the alert module 410 transmits the alert notification to the livestock identification tag 130 of the livestock animal, the alert notification may also include an instruction to activate an indicator (e.g., a visual indicator) of the livestock identification tag 130 as discussed in more detail below.

Figure 5:
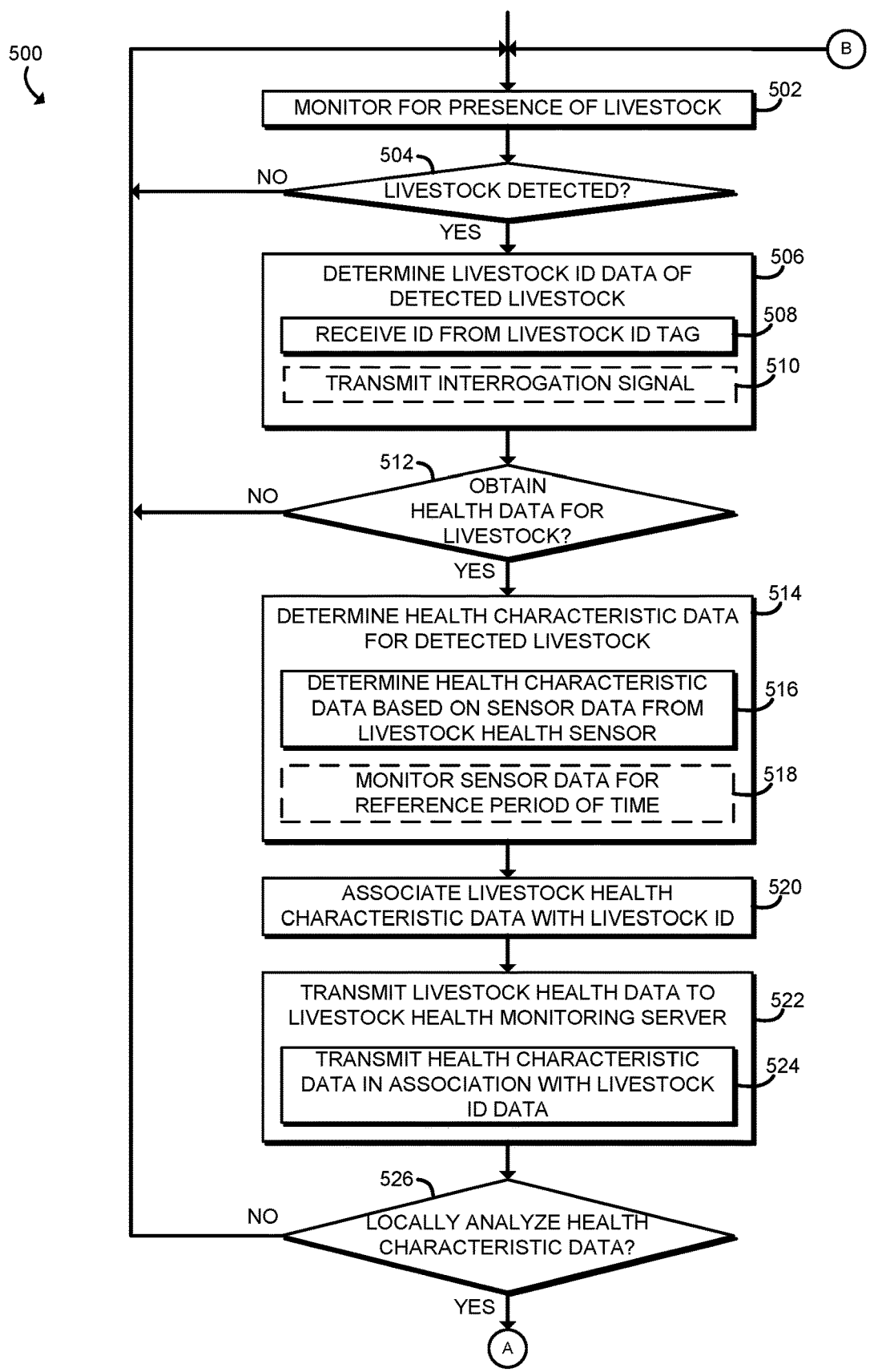
FIGS. 5 and 6 are a simplified flow diagram of at least one embodiment of a method for determining livestock health data of a livestock animal that may be executed by the livestock health sensor system of FIGS. 3 and 4.
Figure 6:
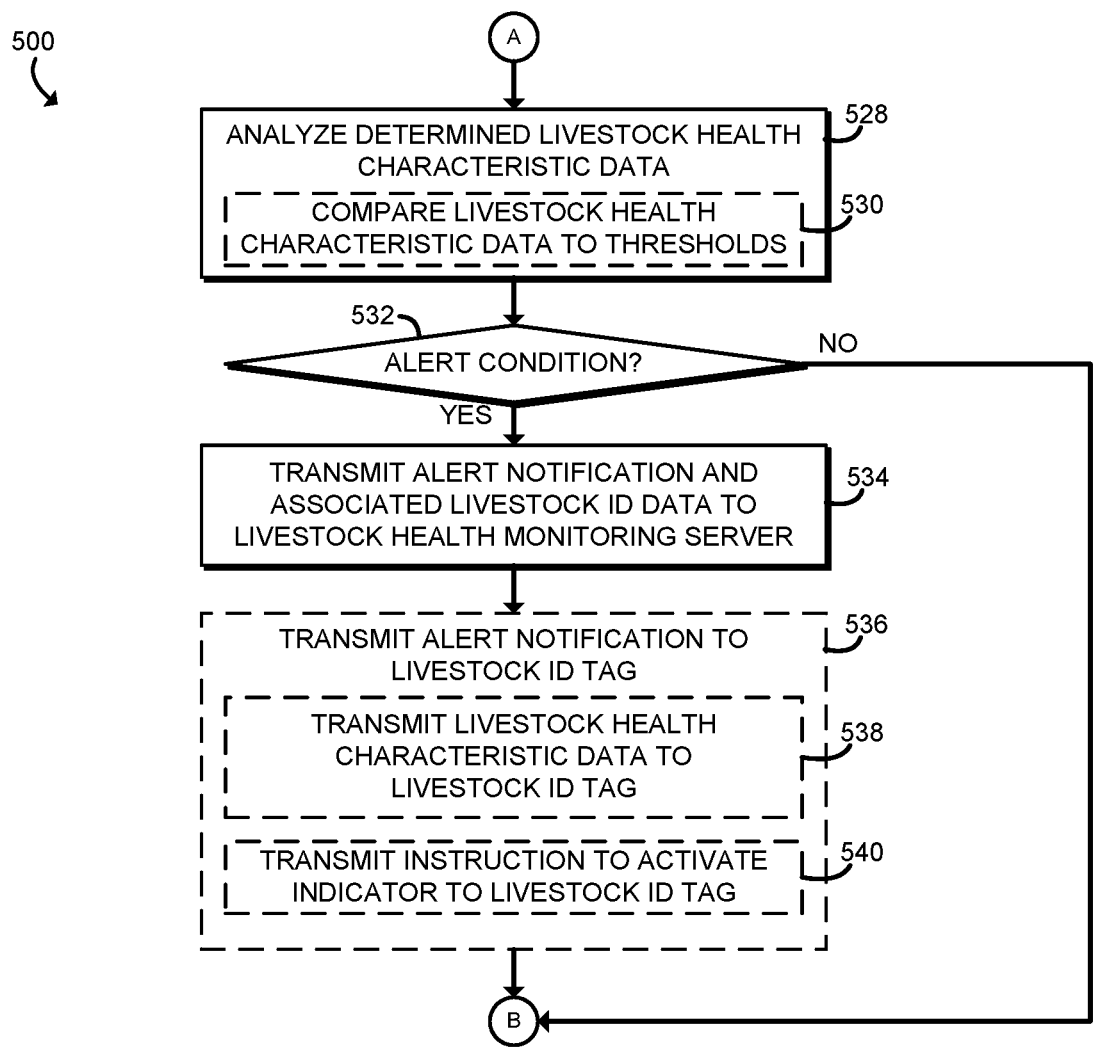

Referring now to FIGS. 5 and 6, in use, each livestock health sensor system 110 may execute a method 500 for determining livestock health data of a livestock animal. The method 500 begins in block 502 in which the livestock health sensor system 110 monitors for the presence of a livestock animal in the vicinity of the livestock health sensor system 110. To do so, as discussed above, the livestock health sensor system 110 may analyze the sensor data produced by the presence sensor 322. In block 504, the livestock health sensor system 110 determines whether the presence of a livestock animal has been detected. If not, the method 500 loops back to block 502 to continue monitoring for the presence of a livestock animal relative to the livestock health sensor system 110. If, however, the presence of a livestock animal is detected, the method 500 advances to block 506. In block 506, the livestock health sensor system 110 determines the livestock identification data of the detected livestock animal. As discussed above, the livestock identification data uniquely identifies the associated livestock animal from other livestock animals of the corresponding herd. Illustratively, the livestock health sensor system 110 determines the livestock identification data of the detected livestock animal by receiving, in block 508, the livestock identification data from the livestock identification tag 130 coupled to the livestock animal. In some embodiments, in block 510, the livestock health sensor system 110 may transmit an interrogation signal to the livestock identification tag 130 of the detected livestock animal to cause the livestock identification tag 130 to transmit the livestock identification data associated with the detected livestock animal.

After the livestock health sensor system 110 has obtained or determined the livestock identification data of the livestock animal, the method 500 advances to block 512. In block 512, the livestock health sensor system 110 determines whether to obtain health data of the detected livestock animal. That is, the livestock health sensor system 110 may continually, periodically, or only responsively determine the health data of the detected livestock animal. For example, some livestock health characteristic data may be obtained or determined only periodically (e.g., once a month) or only in response to a determination that the particular detected livestock animal should be tested.

If the livestock health sensor system 110 determines to obtain health data of the detected livestock animal, the method 500 advances to block 514. In block 514, the livestock health sensor system 110 determines the livestock health characteristic data of the detected livestock animal. To do so, in block 516, the livestock health sensor system 110 may determine the livestock health characteristic data based on the sensor data produced by the livestock health sensor 320. Additionally, in some embodiments in block 518, the livestock health sensor system 110 may monitor the sensor data produced by the livestock health sensor 320 for a period of time to determine the health characteristic data.

After the livestock health sensor system 110 has determined the health characteristic data in block 514, the method 500 advances to block 520 in which the livestock health sensor system 110 associates the livestock health characteristic data with the livestock identification data determined in block 506. The livestock health sensor system 110 subsequently transmits the livestock health data to the livestock health monitoring server 102 in block 522. To do so, the livestock health sensor system 110 transmits the livestock health characteristic data associated with the livestock identification data in block 524.

In block 526, the livestock health sensor system 110 determines whether to locally analyze the determined livestock health characteristic data. As discussed above, in some embodiments, the livestock health sensor system 110 may be embodied as a "smart" sensor system or otherwise include some processing power and functionality. If the livestock health sensor system 110 determines to locally analyze the livestock health characteristic data, the method 500 advances to block 528 of FIG. 6. In block 528, the livestock health sensor system 110 analyzes the determined livestock health characteristic data. To do so, for example, the livestock health sensor system 110 may compare the livestock health characteristic data to various thresholds, trend lines, or other boundaries or expectations in block 530.

In block 532, the livestock health sensor system 110 determines whether the analyzed livestock health characteristic data is abnormal (e.g., based on the comparison to the thresholds). If not, the method 500 loops back to block 502 in which the livestock health sensor system 110 continues to monitor for the presence of other livestock animals. If, however, the livestock health sensor system 110 determines that the analyzed livestock health characteristic data is abnormal, the method 500 advances to block 534. In block 534, the livestock health sensor system 110 transmits an alert notification, which may include the analyzed livestock health characteristic data and associated livestock identification data, to the livestock health monitoring server 102 to inform the server 102 of the detected abnormality of the livestock health characteristic data. Additionally or alternatively, in some embodiments, the livestock health sensor system 110 may transmit an alert notification to the livestock identification tag of the associated livestock animal in block 536. In such embodiments, the livestock health sensor system 110 may transmit the analyzed livestock health characteristic data to the livestock identification tag 130 in block 538 and/or transmit an instruction, which may be included in the alert notification, to the livestock identification tag 130 to instruct the livestock identification tag 130 to activate an indicator of the livestock identification tag 130. For example, the instruction may instruct the livestock identification tag 130 to activate a visual indicator to provide a visual indication that the associated livestock animal may be ill or otherwise should be further monitored.

Figure 7:
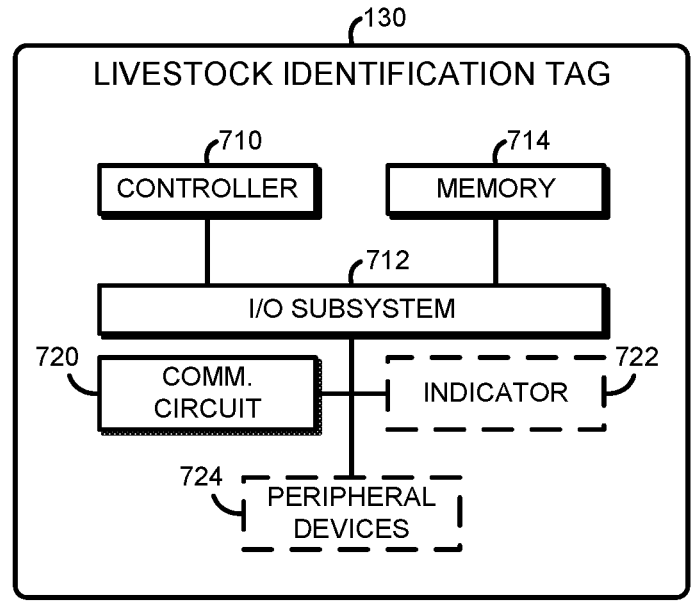
FIG. 7 is a simplified block diagram of at least one embodiment of a livestock identification tag of the system of FIG. 1.

Referring now to FIG. 7, each livestock identification tag 130 may be embodied as any type of identification tag or compute device capable of being attached, implanted, or otherwise coupled to a livestock animal and transmitting identification data that uniquely identifies the livestock animal. For example, the livestock identification tag 130 may be embodied as an ear tag configured to be attached to an ear of the livestock animal or an implantable tag configured to be injected under the skin of the livestock animal. In the illustrative embodiment, the livestock identification tag 130 is embodied as a "smart" tag configured to maintain and transmit livestock identification data, as well as other data. However, in other embodiments, the livestock identification tag 130 may be embodied as a "dumb" tag configured to simply respond to interrogation signals to transmit or broadcast its livestock identification data. For example, in some embodiments, the livestock identification tag 130 may be embodied as a type of radiofrequency identification (RFID) tag.

As shown in FIG. 7, however, each illustrative livestock identification tag 130 includes a controller 710, a memory 714, an I/O subsystem 712, and a communication circuit 720. Of course, the livestock identification tag 130 may include other or additional components, such as those commonly found in identification tags or compute devices, in other embodiments. Additionally, in some embodiments, one or more of the illustrative components may be incorporated in, or otherwise form a portion of, another component. For example, the memory 714, or portions thereof, may be incorporated in the controller 710 in some embodiments.

The controller 710 may be embodied as any type of controller or processor capable of performing the functions described herein. The controller 710 may be embodied as a microcontroller, single or multi-core processor(s), digital signal processor, or other controller, processor, or processing/controlling circuit. Similarly, the memory 714 may be embodied as any type of volatile or non-volatile memory or data storage capable of performing the functions described herein. In operation, the memory 714 may store various data and software used during operation of the livestock identification tag 130. The memory 714 is communicatively coupled to the controller 710 via the I/O subsystem 712, which may be embodied as circuitry and/or components to facilitate input/output operations with the controller 710, the memory 714, and other components of the livestock identification tag 130. For example, the I/O subsystem 712 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 712 may form a portion of a system-on-a-chip (SoC) and be incorporated, along with the controller 710, the memory 714, and other components of the livestock identification tag 130, on a single integrated circuit chip.

The communication circuit 720 of the livestock identification tag 130 may be embodied as any communication circuit, device, or collection thereof, capable of enabling communications between the livestock identification tag 130 and other components of the system 100 including the livestock health sensor systems 110 and the livestock treatment devices 120. To do so, the communication circuit 720 may be configured to use any one or more communication technology (e.g., wired or wireless communications) and associated protocols (e.g., Ethernet, Bluetooth®, Wi-Fi®, WiMAX, WPAN, LoRaWAN, etc.) to effect such communication. In some embodiments, the communication circuitry 720 may include any number of other radio communications equipment, such as transceivers compatible with the Bluetooth® standard as defined by the Bluetooth® special interest group. For example, the communication circuit 720 may communicate over a wireless personal area network (WPAN) according to the IEEE 802.15.4 and IEEE 802.15.4g standards, among others. Additionally or alternatively, the communication circuit 720 may communicate over a wide area using LoRaWAN (Long Range Wide Area Network) developed by Semtech and the LoRa Alliance, Sigfox, and other ultra-narrow band technologies. As discussed in more detail below in regard to FIG. 19, those technologies may be used to establish a mesh network between the example communication circuit 720 and other devices, as well as external networks. Additionally, in some embodiments, the communication circuit 720 be embodied as, or otherwise include communication circuitry capable of responding to an interrogation signal received from a livestock health sensor system 110 and/or a livestock treatment device 120.

In some embodiments, the livestock identification tag 130 may also include one or more indicator 722. The indicator 722 may be embodied as any type of device capable of providing a visual, audible, or tactile indication. For example, in some embodiments, the indicator 722 may be embodied as a visual indicator, such as a light emitting diode (LED) and associated circuitry, configured to provide a visual indication (e.g., by blinking). As discussed in more detail below, the indicator 722 may be activated by the livestock identification tag 130 to provide an indication that the associated livestock animal has abnormal health characteristic data, is sick, or is otherwise under observation.

In some embodiments, the livestock identification tag 130 may also include one or more other peripheral devices 724. Such peripheral devices 724 may be embodied as any type of device or component commonly found in an identification tag or similar device such as output devices or input devices.

Figure 8:
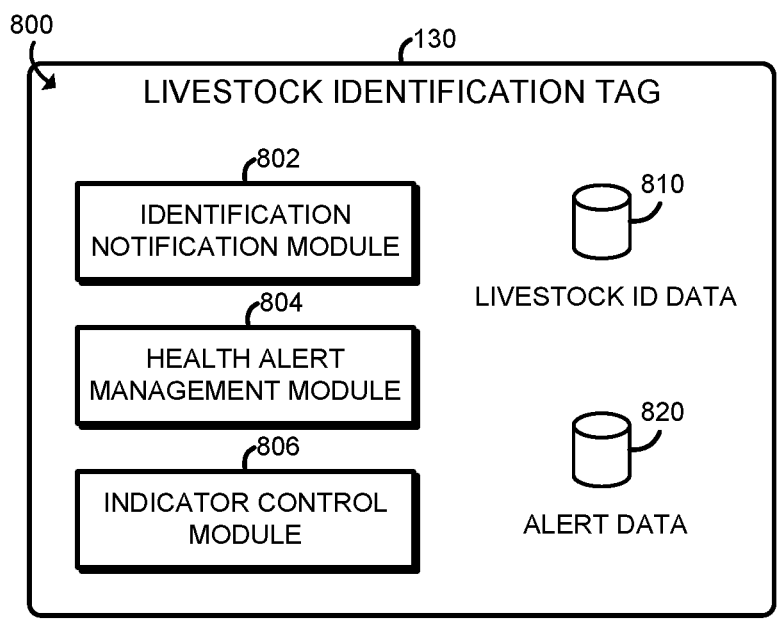
FIG. 8 is a simplified block diagram of at least one embodiment of an environment that may be established by the livestock identification tag of FIG. 7.

Referring now to FIG. 8, in use, each livestock identification tag 130 may establish an environment 800. The illustrative environment 800 includes an identification notification module 802, a health alert management module 804, and an indicator control module 806. Each of the modules, logic, and other components of the environment 400 may be embodied as hardware, firmware, software, or a combination thereof. As such, in some embodiments, one or more of the modules of the environment 800 may be embodied as circuitry or collection of electrical devices (e.g., an identification notification circuit 802, a health alert management circuit 804, a circuit control module 806, etc.). It should be appreciated that, in such embodiments, one or more of the an identification notification circuit 802, the health alert management circuit 804, and/or the circuit control module 806 may form a portion of one or more of the controller 710, the memory 714, the I/O subsystem 712, the communication circuit 720, and/or other components of the livestock identification tag 130. Additionally, in some embodiments, one or more of the illustrative modules may form a portion of another module and/or one or more of the illustrative modules may be independent of one another. Further, in some embodiments, one or more of the modules of the environment 800 may be embodied as virtualized hardware components or emulated architecture, which may be established and maintained by the controller 710 or other components of the livestock identification tag 130.

The identification notification module 802 is configured to transmit a livestock identification data 810, which uniquely identifies the associated livestock animal, to other components of the system 100 via the communication circuit 720. The livestock identification data 810 may be stored in the memory 714 (e.g., non-volatile or immutable memory). In some embodiments, the livestock identification data or number 810 is assigned to each livestock animal at birth. Additionally, the livestock identification data 810 may be permanently assigned (i.e., does not change over time). In some embodiments, the identification notification module 802 is configured to retrieve the livestock identification data 810 from the memory 714 and transmit the livestock identification data 810 in response to receipt of an interrogation signal or other communication from a livestock health sensor system 110 or a livestock treatment device 120. In other embodiments, the identification notification module 802 may periodically or continually broadcast the identification notification module 802.

The health alert management module 804 is configured to manage alert notifications received from a livestock health sensor system 110, the livestock health monitoring server 102. In some embodiments, the alert notifications may include alert data 820 that is to be stored by the livestock identification tag 130 (e.g., in the memory 714 or a data storage). For example, in some embodiments, an alert notification may include livestock health characteristic data, which may have been determined to be abnormal, that is to be stored on the livestock identification tag 130. Additionally, as discussed above, the alert notifications may include an instruction to activate the indicator 722 of the livestock identification tag 130. In such embodiments, the indicator control module 806 is configured to control the activation of the indicator 722 pursuant to the instructions. The activation instructions may dictate, for example, the type of indicator control to be used (e.g., blinking or steady activation), the length of time the indicator 722 is to be activated, and so forth.

Figure 9:
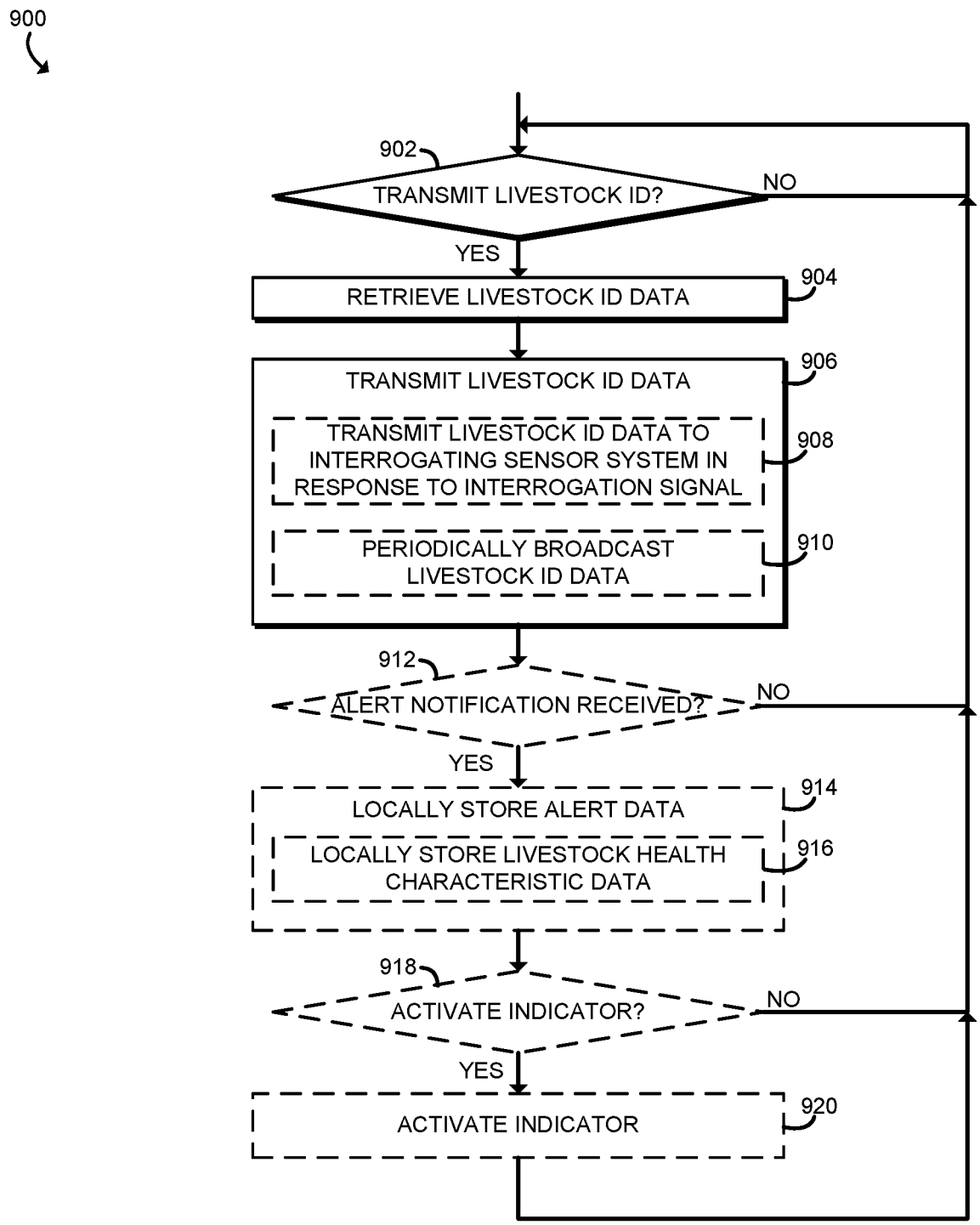
FIG. 9 is a simplified flow diagram of at least one embodiment of a method for providing an identity of a livestock animal that may be executed by the livestock identification tag of FIGS. 7 and 8.

Referring now to FIG. 9, in use, each livestock identification tag 130 may execute a method 900 for providing an identity of a livestock animal. The method 900 begins with block 902 in which the livestock identification tag 130 determines whether to transmit the livestock identification data maintained by that particular livestock identification tag 130. As discussed above, in some embodiments, the livestock identification tag 130 may receive an interrogation signal or other communication from a livestock health sensor system 110 or a livestock treatment device 120. In such embodiments, the livestock identification tag 130 may determine to transmit the livestock identification data in response to the interrogation signal or other communication. Alternatively, in other embodiments, the livestock identification tag 130 may periodically or continually transmit or broadcast the livestock identification data.

Regardless, if the livestock identification tag 130 determines to transmit the livestock identification data, the method 900 advances to block 904 in which the livestock identification tag 130 retrieves the livestock identification data from the memory 714 or other storage location. The livestock identification tag 130 subsequently transmits the livestock identification data in block 906. For example, in block 908, the livestock identification tag 130 may transmit the livestock identification data in response to a received interrogation signal. Alternatively, in block 910, the livestock identification tag 130 may periodically broadcast or transmit the livestock identification data.

After the livestock identification tag 130 has transmitted the livestock identification data in block 906, the method 900 advances to block 912 in some embodiments. In block 912, the livestock identification tag 130 determines whether an alert notification has been received. For example, an alert notification may be received from a livestock health sensor system 110, from the livestock health monitoring server 102, or from a livestock treatment device 120. If not, the method 900 loops back to block 902 in which the livestock identification tag 130 determine whether to transmit the livestock identification data again.

If, however, an alert notification has been received, the method 900 advances to block 914 in which the livestock identification tag 130 locally stores the alert data included in the alert notification. For example, the livestock identification tag 130 may store livestock health characteristic data included in the alert notification in block 916. The livestock identification tag 130 may store the alert data in the memory 714 or other data storage of the livestock identification tag 130.

In block 918, the livestock identification tag 130 determines whether to activate an indicator 722 of the livestock identification tag 130. As discussed above, the alert notification may include an instruction to activate the indicator 722 in some embodiments. If so, the method 900 advances to block 920 in which the livestock identification tag 130 activates the indicator pursuant to the received activation instructions. As discussed above, the activation instructions may dictate how the indicator 722 is to be activated (e.g., the length of activation time, the rate of activation sequences, etc.). After the livestock identification tag 130 has activated the indicator 722, the method 900 loops back to block 902 in which the livestock identification tag 130 determine whether to transmit the livestock identification data again.

Figure 10:
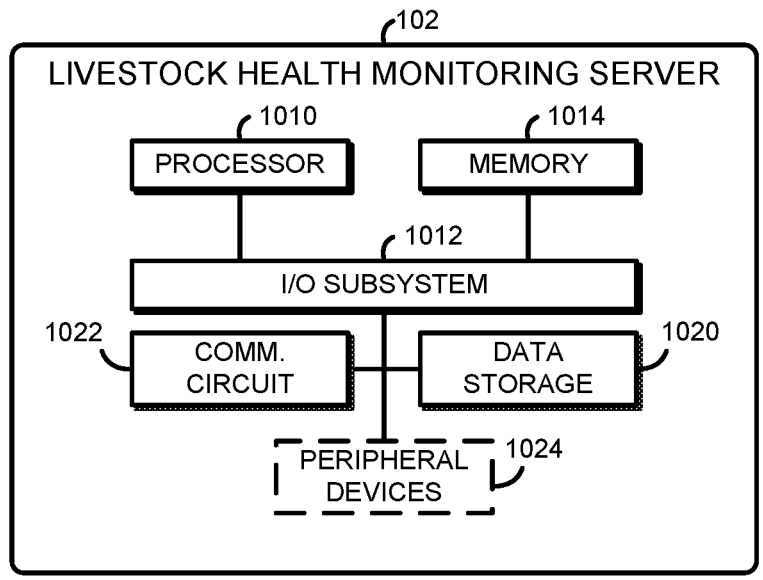
FIG. 10 is a simplified block diagram of at least one embodiment of a livestock health monitoring server of the system of FIG. 1.

Referring now to FIG. 10, the livestock health monitoring server 102 may be embodied as any type of server compute device capable of monitoring health data of livestock animals and performing the functions described herein. For example, in some embodiments, the livestock health monitoring server 102 may be embodied as, without limitation, a server computer, a distributed computing system, a multi-processor system, a consumer electronic device, a smart appliance, and/or any other computing device capable of performing the functions described herein. Although shown as a single compute device, it should be appreciated that the livestock health monitoring server 102 may be embodied as a collection of servers and/or other compute devices configured to cooperate to perform the functions described herein. For example, in some embodiments, the functionality of the livestock health monitoring server 102 may be performed in a cloud environment by distributed servers or other compute devices.

As shown in FIG. 10, the illustrative livestock health monitoring server 102 includes a processor 1010, a memory 1014, an input/output subsystem 1012, a data storage 1020, and a communication circuit 1022. Of course, the livestock health monitoring server 102 may include other or additional components, such as those commonly found in a server compute device (e.g., various input/output devices, data storage device(s), etc.), in other embodiments. Additionally, in some embodiments, one or more of the illustrative components may be incorporated in, or otherwise from a portion of, another component. For example, the memory 1014, or portions thereof, may be incorporated in the processor 1010 in some embodiments.

The processor 1010 may be embodied as any type of processor capable of performing the functions described herein. For example, the processor may be embodied as a single or multi-core processor(s) having one or more processor cores, a digital signal processor, a microcontroller, or other processor or processing/controlling circuit. Similarly, the memory 1014 may be embodied as any type of volatile or non-volatile memory or data storage capable of performing the functions described herein. In operation, the memory 1014 may store various data and software used during operation of the livestock health monitoring server 102 such as livestock health data. The memory 1014 is communicatively coupled to the processor 1010 via the I/O subsystem 1012.

The I/O subsystem 1012 may be embodied as circuitry and/or components to facilitate input/output operations with the processor 1010, the memory 1014, and other components of the 1012. For example, the I/O subsystem 1012 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 1012 may form a portion of a system-on-a-chip (SoC) and be incorporated, along with the processor 1010, the memory 1014, and other components of the livestock health monitoring server 102, on a single integrated circuit chip.

The data storage 1020 may be embodied as any type of device or devices configured for short-term or long-term storage of data such as, for example, memory devices and circuits, memory cards, hard disk drives, solid-state drives, or other data storage devices. As described further below, the data storage device 1020 may store livestock health data received from the livestock health sensor systems 110 and/or other data.

The communication circuit 1022 of the livestock health monitoring server 102 may be embodied as any communication circuit, device, or collection thereof, capable of enabling communications between the livestock health monitoring server 102 and other components of the system 100 such as the livestock health sensor systems 110, the livestock treatment devices 120, and/or the livestock identification tags 130. The communication circuit 1022 may be configured to use any one or more communication technology (e.g., wired or wireless communications) and associated protocols (e.g., Ethernet, Bluetooth®, Wi-Fi®, WiMAX, WPAN, LoRaWAN, etc.) to effect such communication. In some embodiments, the communication circuitry 1022 may include any number of other radio communications equipment, such as transceivers compatible with the Bluetooth® standard as defined by the Bluetooth® special interest group. For example, the communication circuit 1022 may communicate over a wireless personal area network (WPAN) according to the IEEE 802.15.4 and IEEE 802.15.4g standards, among others. Additionally or alternatively, the communication circuit 1022 may communicate over a wide area using LoRaWAN (Long Range Wide Area Network) developed by Semtech and the LoRa Alliance, Sigfox, and other ultra-narrow band technologies. As discussed in more detail below in regard to FIG. 19, those technologies may be used to establish a mesh network between the example communication circuit 1022 and other devices, as well as external networks.

In some embodiments, the livestock health monitoring server 102 may also include one or more other peripheral devices 1024. Such peripheral devices 1024 may be embodied as any type of device or component commonly found in a sever compute device such as output devices or input devices.

Figure 11:
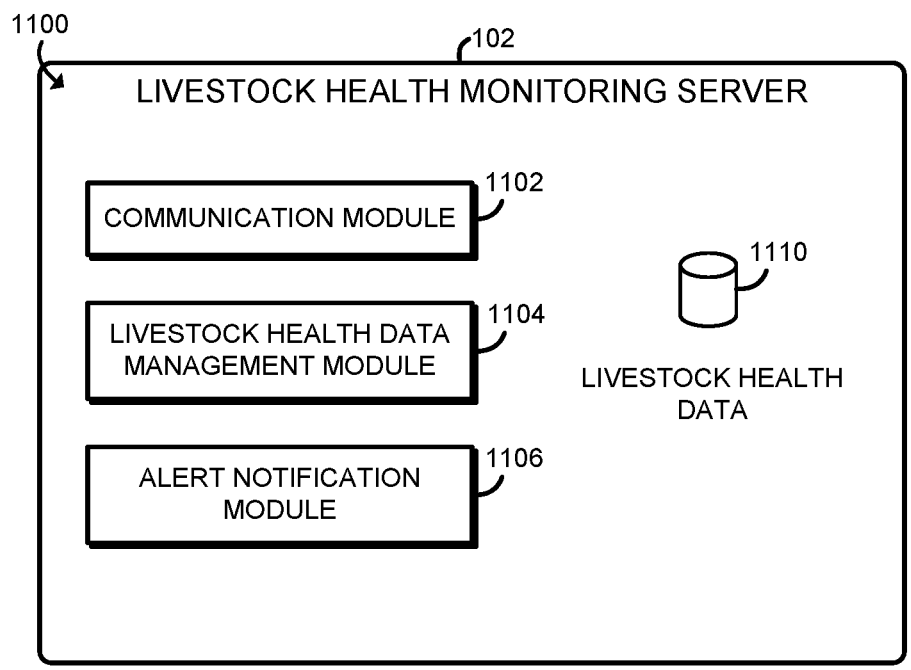
FIG. 11 is a simplified block diagram of at least one embodiment of an environment that may be established by the livestock health monitoring server of FIG. 10.

Referring now to FIG. 11, in use, the livestock health monitoring server 102 may establish an environment 1100. The illustrative environment 1100 includes a communication module 1102, a livestock health data management module 1104, and an alert notification module 1106. Each of the modules, logic, and other components of the environment 1100 may be embodied as hardware, firmware, software, or a combination thereof. As such, in some embodiments, one or more of the modules of the environment 1100 may be embodied as circuitry or collection of electrical devices (e.g., a communication circuit 1102, a livestock health data management circuit 1104, an alert notification circuit 1106, etc.). It should be appreciated that, in such embodiments, one or more of the communication circuit 1102, the livestock health data management circuit 1104, and/or the alert notification circuit 1106 may form a portion of one or more of the processor 1010, the memory 1014, the I/O subsystem 1012, the data storage 1020, the communication circuit 1022, and/or other components of the livestock health monitoring server 102. Additionally, in some embodiments, one or more of the illustrative modules may form a portion of another module and/or one or more of the illustrative modules may be independent of one another. Further, in some embodiments, one or more of the modules of the environment 1100 may be embodied as virtualized hardware components or emulated architecture, which may be established and maintained by the processor 1010 or other components of the livestock health monitoring server 102.

The communication module 1102 enables communications of the livestock health monitoring server 102 with other components of the system 100, such as the livestock health sensor systems 110, the livestock treatment devices 120, and/or the livestock identification tags 130, via the communication circuit 1022. For example, the communication module 1102 receives the livestock health data from the livestock health sensor systems 110 during operation of the system 100 and locally stores the health data as livestock health data 1110 in the storage 1020 and/or memory 1014. Additionally, as discussed below, the communication module 1102 may facilitate the transmission of alert notifications from the livestock health monitoring server 102.

The livestock health data management module 1104 is configured to manage the livestock health data received from the livestock health sensor systems 110 and analyze the health data. As discussed above, the livestock health data includes livestock health characteristic data indicative of a health characteristic of a livestock animal and an associated livestock identification data that uniquely identifies that livestock animal. As such, the livestock health data management module 1104 is configured to maintain and track the livestock health characteristic data of each livestock animal based on the unique livestock identification data assigned to the livestock animals. For each livestock animal, the livestock health data management module 1104 may maintain and track any number of livestock characteristics depending on, for example, the type of livestock health sensor systems 110 used in the system 110. Additionally, the livestock health monitoring server 102 may maintain and track the livestock health characteristic data over the course of the life of each livestock animal, creating a life-long health report for the livestock animals.

The livestock health data management module 1104 is also configured to analyze the livestock health characteristic data to determine whether any abnormalities are present. To do so, the livestock health monitoring server 102 may analyze new livestock health characteristic data as it is received from livestock health sensor systems 110. For example, the livestock health data management module 1104 may compare the livestock health characteristic data to thresholds or ranges to determine whether any newly received livestock health characteristic data is outside the normal or expected ranges or behavior. Additionally or alternatively, the livestock health data management module 1104 may aggregate any newly received livestock health characteristic data with historical livestock health characteristic data to determine trends in the livestock health characteristic data of the livestock animals. The livestock health data management module 1104 may subsequently analyze such trends for abnormalities or indications of future predicted health issues. In some embodiments, the livestock health data management module 1104 may determine abnormalities in the livestock health characteristic data of a livestock animal by comparing the livestock health characteristic data of that livestock animal to livestock health characteristic data of other livestock animals of the same herd (e.g., is the livestock animal eating the same amount, gaining the same weight, moving the same manner, etc.).

If the livestock health data management module 1104 determines that there is an abnormality or concern with any the livestock health characteristic data of any livestock animal, the alert module 410 may generate an alert notification, which the alert module 410 may transmit to the livestock health sensor systems 110, the livestock treatment devices 120, and/or the livestock identification tags 130. In some embodiments, the alert notification may include a treatment list that identifies the livestock identification data of all livestock animals that are determined to have abnormal livestock health characteristic data. In such embodiments, the livestock treatment devices 120 may provide treatment (e.g., quarantine, medicine distribution, etc.) to the identified livestock animals based on the livestock treatment list. In other embodiments, the alert notification may be transmitted on a per-animal basis and include the livestock identification data of a single livestock animal, along with any other data (e.g., the livestock health characteristic data and/or instructions). For example, if the alert module 410 transmits the alert notification to a livestock identification tag 130, the alert notification may include an instruction to activate an indicator 722 of the livestock identification tag 130.

In some embodiments, the alert notification module 1106 may also be configured to send an alert notification to a personal compute device 150 of a user (e.g., a farmer or livestock owner) of the system 100 over an external network 140 (see FIG. 1). In this way, the livestock health monitoring server 102 may alert individual users or related workers to potential health issues related to the livestock animals. In such embodiments, the personal compute device 150 may be embodied as any type of compute device capable of receiving communications from the livestock health monitoring server 102 and providing notifications to the user. For example, the personal, compute device 150 may be embodied as a smart phone, a tablet compute device, a mobile compute device, a laptop compute device, a desktop compute device, or other personal compute device. The personal compute device 150 may include components, such as a processor, memory, communication circuit, and a display, commonly found in such personal compute devices.

Similar to the local network 108, the external network 140 may be embodied as any type of network capable of facilitating communications between the components of the system 100. For example, the networks 108, 140 may be embodied as, or otherwise include, a wired or wireless local area network (LAN), a wired or wireless wide area network (WAN), a cellular network, and/or a publicly-accessible, global network such as the Internet. As such, the networks 108, 140 may include any number of additional devices, such as additional computers, routers, and switches, to facilitate communications among the devices of the system 100.

Figure 12:
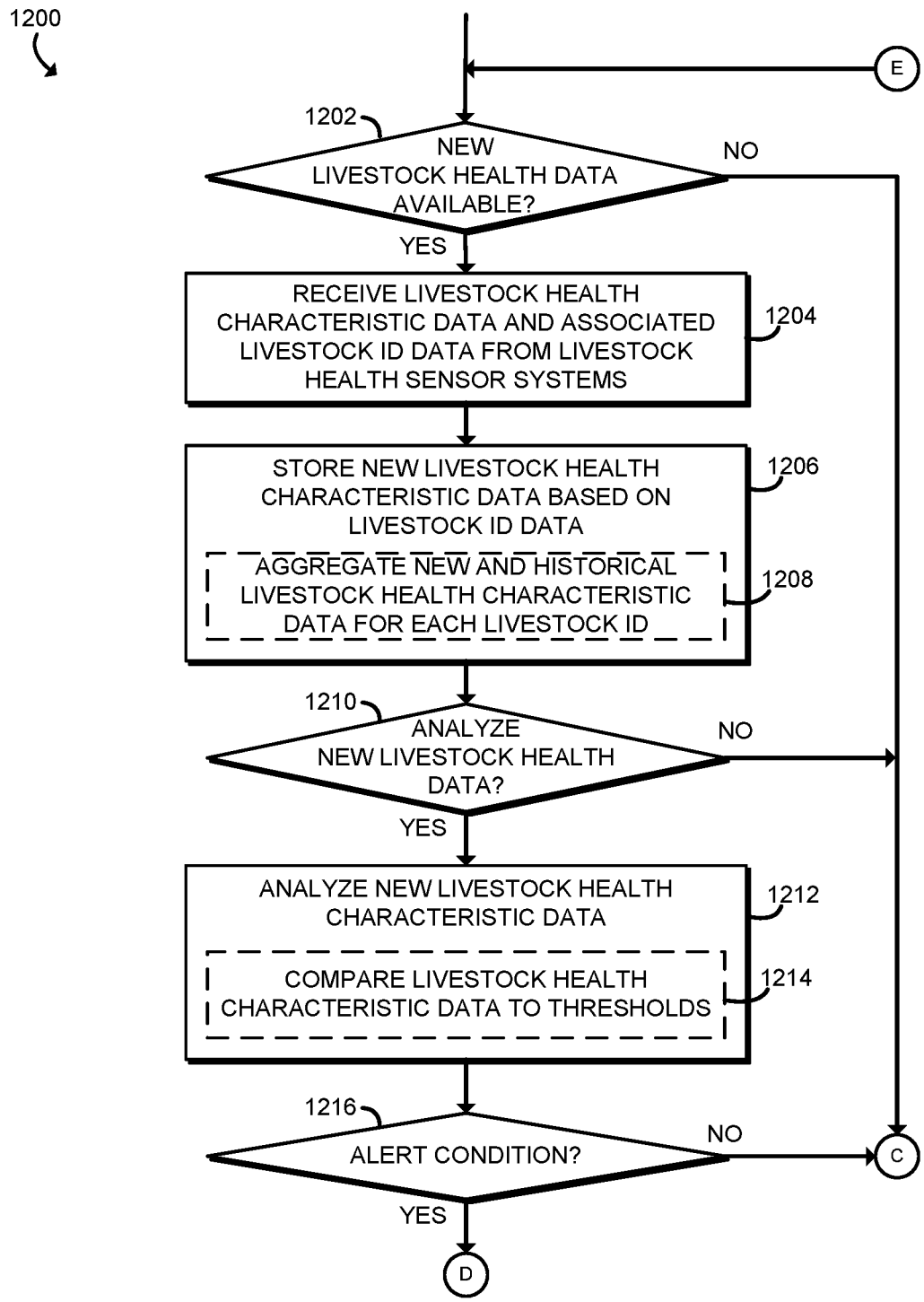
FIGS. 12 and 13 are a simplified flow diagram of at least one embodiment of a method for managing livestock health data that may be executed by the livestock health monitoring server of FIGS. 10 and 11.
Figure 13:
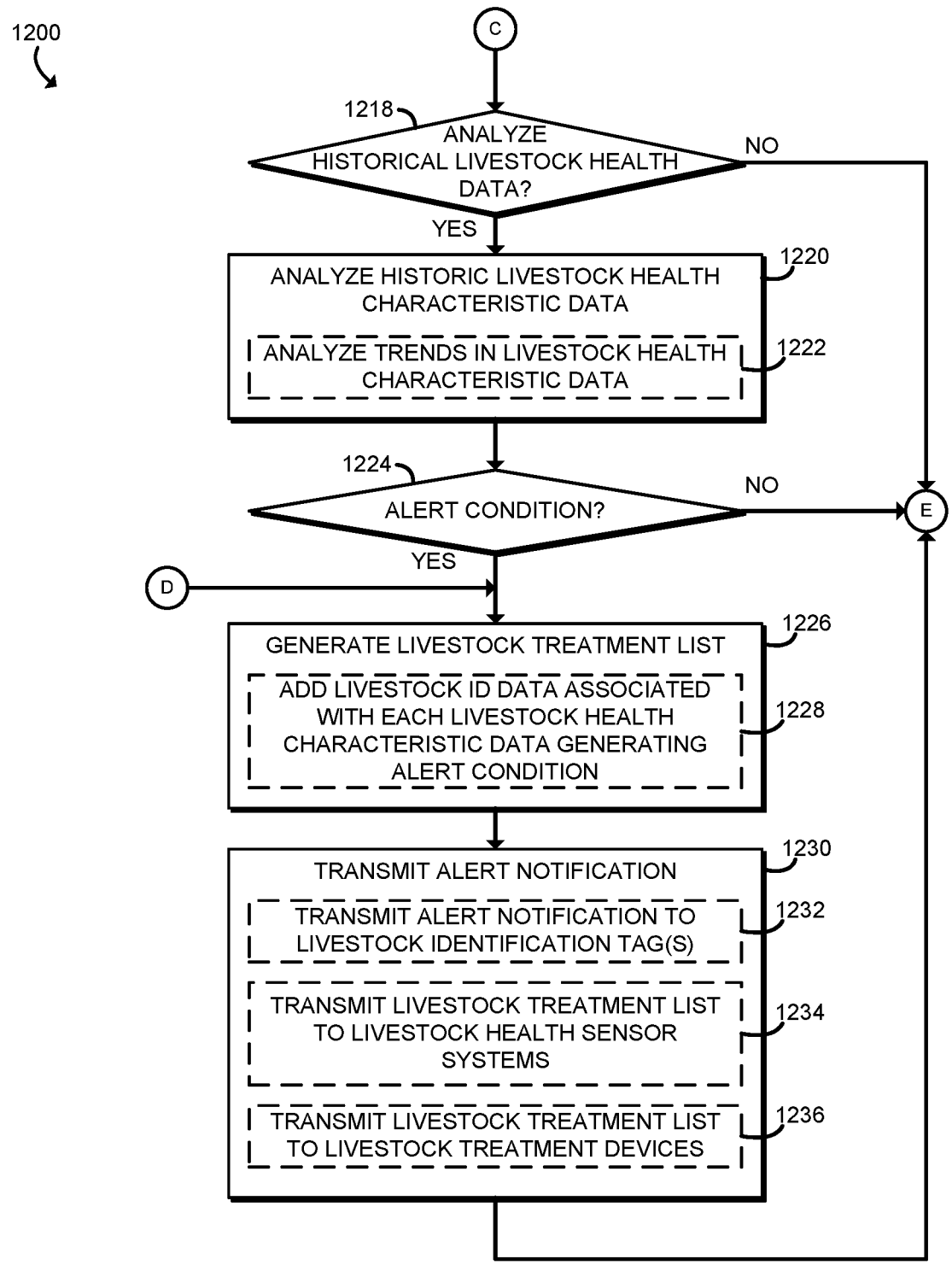

Referring now to FIGS. 12 and 13, in use, the livestock health monitoring server 102 may execute a method 1200 for managing livestock health data. The method 1200 begins with block 1202 in which the livestock health monitoring server 102 determines whether new livestock health data has been received from one or more livestock health sensor system 110. If so, the method 1200 advances to block 1204 in which the livestock health monitoring server 102 receives the livestock health data from the livestock health sensor system 110. As discussed above, the livestock health data includes livestock health characteristic data indicative of a health characteristic of a livestock animal associated with livestock identification data the uniquely identifies that livestock animal. Subsequently, in block 1206, the livestock health monitoring server 102 stores the newly received health data in the data storage 1020 and/or memory 1014. In some embodiments, in block 1208, the livestock health monitoring server 102 may aggregate the new livestock health characteristic data with existing, historical livestock health characteristic data based on the livestock identification data associated with the data.

After the livestock health monitoring server 102 has stored the livestock health data, the method 1200 advances to block 1210 in which the livestock health monitoring server 102 determines whether to analyze the newly received livestock health characteristic data. As discussed above, the livestock health monitoring server 102 may be configured to analyze new livestock health characteristic data and/or historical livestock health characteristic data. If the livestock health monitoring server 102 determines to analyze the newly received livestock health characteristic data in block 1210, the method 1200 advances to block 1212. In block 1212, the livestock health monitoring server 102 analyzes the newly received livestock health characteristic data. To do so, the livestock health monitoring server 102 may utilize any suitable analysis methodology or technique. For example, in some embodiments, the livestock health monitoring server 102 may analyze the newly received livestock health characteristic data by comparing the livestock health characteristic data to thresholds or ranges in block 1214.

Regardless, based on such analysis, the livestock health monitoring server 102 determines whether an alert condition is present indicative that the livestock health characteristic data is abnormal or otherwise unexpected in block 1216. If so, the method 1200 advances to block 1226 of FIG. 13 discussed below. If no alert condition is present, however, the method 1200 advances to block 1218 of FIG. 13. In block 1218, the livestock health monitoring server 102 determines whether to analyze the historical livestock health characteristic data. As discussed above, the livestock health monitoring server 102 may be configured to analyze new livestock health characteristic data and/or historical livestock health characteristic data. If the livestock health monitoring server 102 determines to analyze the historical livestock health characteristic data in block 1218, the method 1200 advances to block 1220. In block 1220, the livestock health monitoring server 102 analyzes the historical livestock health characteristic data associated with one or more livestock animals. To do so, the livestock health monitoring server 102 may utilize any suitable analysis methodology or technique. For example, in some embodiments in block 1222, the livestock health monitoring server 102 may analyze identified trends in the historical livestock health characteristic data to identify present abnormalities or otherwise predict possible future abnormalities in the livestock health characteristic data of each analyzed livestock animal. It should be appreciated the livestock health monitoring server 102 may analyze the historical livestock health characteristic data of any or all monitored livestock animals continually, periodically, or in response to some event (e.g., detection of an abnormality in one livestock animal may cause the livestock health monitoring server 102 to perform an analysis of the historical livestock health characteristic data of other livestock animals of the same herd).

Based on the historical analysis, the livestock health monitoring server 102 determines whether an alert condition is present indicative that the historical livestock health characteristic data is abnormal or otherwise unexpected in block 1224. If the livestock health monitoring server 102 determines that an alert condition is present in either of blocks 1216 or 1224, the method 1200 advances to block 1226. In block 1226, the livestock health monitoring server 102 generates a livestock treatment list. To do so, in block 1228, the livestock health monitoring server 102 adds or appends the livestock identification data associated with the identified abnormal livestock health characteristic data. As such, the livestock treatment list identifies each livestock animal determined to be ill, suspicious of being ill, or otherwise requiring monitoring or supervision.

In block 1230, the livestock health monitoring server 102 transmits an alert notification to one or more components of the system 100. For example, in block 1232, the livestock health monitoring server 102 may transmit the alert notification to the livestock identification tag 130 of each livestock animal included in the livestock treatment list. In such embodiments, the alert notification may include the abnormal livestock health characteristic data and/or an instruction to active the indicator 722 of the livestock identification tag 130. Additionally or alternatively, in block 1234, the livestock health monitoring server 102 may transmit the livestock treatment list to one or more livestock health sensor systems 110. In such embodiments, the livestock health sensor systems 110 may utilize the livestock treatment list to identify those livestock animals for with additional livestock health data is required and continue providing the livestock health monitoring server 102 with such health data. Additionally or alternatively, in block 1234, the livestock health monitoring server 102 may transmit the livestock treatment list to one or more livestock treatment devices 120. In such embodiments, the livestock treatment devices 120 utilize the livestock treatment list to identify those livestock animals to which a health treatment is to be applied or supplied. As discussed in more detail below, such health treatments may include quarantining the livestock animal, dispensing medicine to the livestock animal, and so forth.

Figure 14:
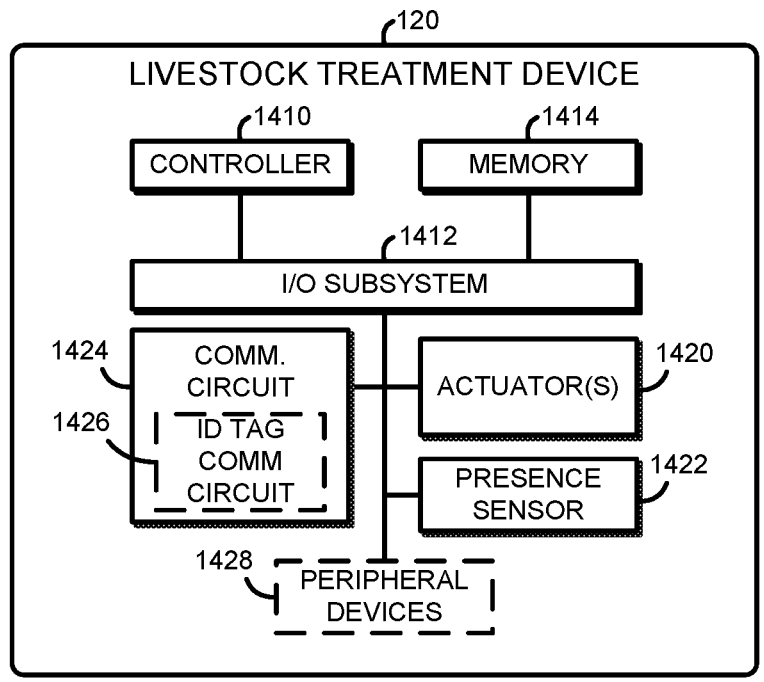
FIG. 14 is a simplified block diagram of at least one embodiment of a livestock treatment device of the system of FIG. 1.

Referring now to FIG. 14, each livestock treatment device 120 may be embodied as any type of device capable of providing a health treatment or action to a livestock animal. For example, the livestock treatment devices 120 may be embodied as gate control devices, medicine dispensers, injection devices, mist sprayers, and/or any other type of device capable of providing a medical treatment (including quarantining) to a livestock animal. The illustrative livestock treatment device 120 is embodied as a "smart" treatment device configured to provide treatment to a livestock animal based on various data (e.g., instructions received from the livestock health monitoring server 102). However, in other embodiments, one or more of the livestock treatment devices 120 of the system 100 may be embodied as "dumb" treatment devices having few components and configured to be directly controlled by livestock health monitoring server 102 (e.g., a gate actuator directly controlled by the livestock health monitoring server 102).

As shown in FIG. 14, each livestock treatment device 120 illustratively includes a controller 1410, a memory 1414, an I/O subsystem 1412, one or more actuators 1420, a presence sensor 1422, and a communication circuit 1424. Of course, the livestock treatment device 120 may include other or additional components, such as those commonly found in a treatment device, in other embodiments. Additionally, in some embodiments, one or more of the illustrative components may be incorporated in, or otherwise form a portion of, another component. For example, the memory 1414, or portions thereof, may be incorporated in the controller 1410 in some embodiments.

The controller 1410 may be embodied as any type of controller or processor capable of performing the functions described herein. The controller 1410 may be embodied as a microcontroller, single or multi-core processor(s), digital signal processor, or other controller, processor, or processing/controlling circuit. Similarly, the memory 1414 may be embodied as any type of volatile or non-volatile memory or data storage capable of performing the functions described herein. In operation, the memory 1414 may store various data and software used during operation of the livestock treatment device 120. The memory 1414 is communicatively coupled to the controller 1410 via the I/O subsystem 1412, which may be embodied as circuitry and/or components to facilitate input/output operations with the controller 1410, the memory 1414, and other components of the livestock treatment device 120. For example, the I/O subsystem 1412 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 1412 may form a portion of a system-on-a-chip (SoC) and be incorporated, along with the controller 1410, the memory 1414, and other components of the livestock treatment device 120, on a single integrated circuit chip.

The actuator 1420 may be embodied as any type of actuator, motor, or other device controllable by the livestock treatment device 120 depending on the type of treatment the livestock treatment device 120 is configured to supply. For example, the actuator 1320 may be embodied as a linear actuator for controlling a sorting gate, a stepper motor for injecting a medicine into a livestock animal, an electronic lock or lid for dispensing medicine into the food of a livestock animal, and/or other types of controllable or movable actuators.

Similar to the presence sensor 322 of the livestock health sensor system 110, the presence sensor 1422 may be embodied as any type of sensor or sensing circuit capable of producing sensor data indicative of a presence of a livestock animal in the vicinity of the corresponding livestock treatment device 120. For example, in some embodiments, the presence sensor 1422 may be embodied as an infra-red sensor, a weight sensor, a camera, a motion detector, a communication circuit, or other sensor or sensing circuit capable of detecting the presence of a livestock animal. In some embodiments, the presence sensor 1422 may sense or detect the presence of a livestock animal based on transmissions (e.g., broadcasts) received from a livestock identification tag 130 attached to the corresponding livestock animal.

The communication circuit 1424 of the livestock treatment device 120 may be embodied as any communication circuit, device, or collection thereof, capable of enabling communications between the livestock treatment device 120 and other components of the system 100 such as the livestock health monitoring server 102 and/or the livestock identification tags 130. The communication circuit 1424 may be configured to use any one or more communication technology (e.g., wired or wireless communications) and associated protocols (e.g., Ethernet, Bluetooth®, Wi-Fi®, WiMAX, WPAN, LoRaWAN, etc.) to effect such communication. In some embodiments, the communication circuitry 1424 may include any number of other radio communications equipment, such as transceivers compatible with the Bluetooth® standard as defined by the Bluetooth® special interest group. For example, the communication circuit 1424 may communicate over a wireless personal area network (WPAN) according to the IEEE 802.15.4 and IEEE 802.15.4g standards, among others. Additionally or alternatively, the communication circuit 1424 may communicate over a wide area using LoRaWAN (Long Range Wide Area Network) developed by Semtech and the LoRa Alliance, Sigfox, and other ultra-narrow band technologies. As discussed in more detail below in regard to FIG. 19, those technologies may be used to establish a mesh network between the example communication circuit 1424 and other devices, as well as external networks.

In some embodiments, the communication circuit 1424 may include an identification tag communication circuit 1426 configured to transmit or broadcast an interrogation signal to the livestock identification tags 130 to cause the livestock identification tags 130 to transmit their respective livestock identification data. For example, in some embodiments, the identification tag communication circuit 1426 may be embodied as or otherwise include a radio-frequency identification (RFID) transmission circuit.

In some embodiments, the livestock treatment device 120 may also include one or more other peripheral devices 1428. Such peripheral devices 1428 may be embodied as any type of device or component commonly found in a medical treatment device such as output devices or input devices.

Figure 15:
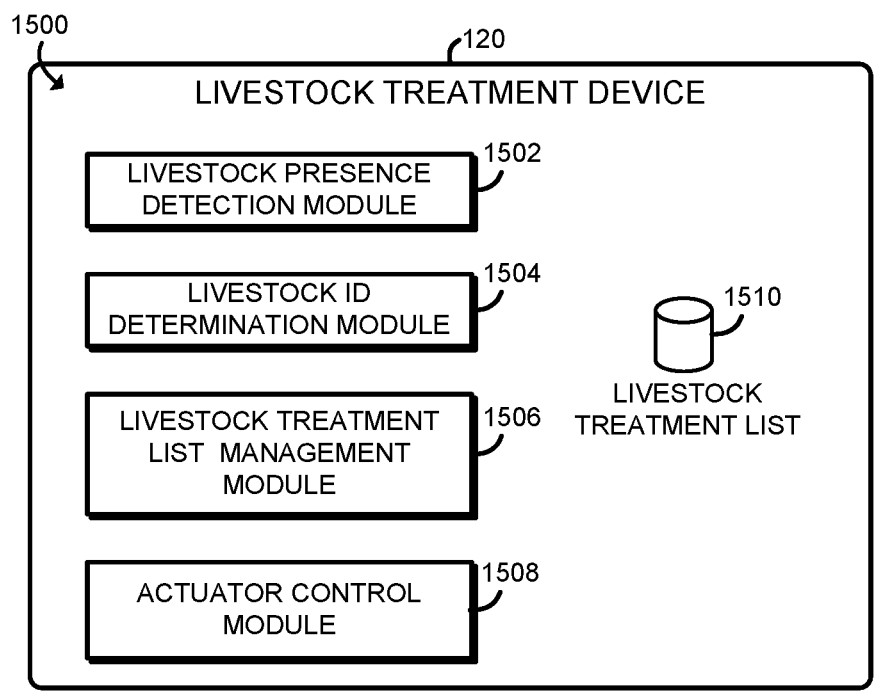
FIG. 15 is a simplified block diagram of at least one embodiment of an environment that may be established by the livestock treatment device of FIG. 14.

Referring now to FIG. 15, in use, each livestock treatment device 120 may establish an environment 1500. The illustrative environment 1500 includes a livestock presence detection module 1502, a livestock identification determination module 1504, a livestock treatment list management module 1506, and an actuator control module 1508. Each of the modules, logic, and other components of the environment 1500 may be embodied as hardware, firmware, software, or a combination thereof. As such, in some embodiments, one or more of the modules of the environment 1500 may be embodied as circuitry or collection of electrical devices (e.g., a livestock presence detection circuit 1502, a livestock identification determination circuit 1504, a livestock treatment list management circuit 1506, an actuator control circuit 1508, etc.). It should be appreciated that, in such embodiments, one or more of the livestock presence detection circuit 1502, the livestock identification determination circuit 1504, the livestock treatment list management circuit 1506, and/or the actuator control circuit 1508 may form a portion of one or more of the controller 1310, the memory 1314, the I/O subsystem 1312, the actuator 1320, the presence sensor 1322, the communication circuit 1324, and/or other components of the livestock treatment device 120. Additionally, in some embodiments, one or more of the illustrative modules may form a portion of another module and/or one or more of the illustrative modules may be independent of one another. Further, in some embodiments, one or more of the modules of the environment 1500 may be embodied as virtualized hardware components or emulated architecture, which may be established and maintained by the controller 1310 or other components of the livestock treatment device 120.

The livestock presence detection module 1502 is configured to determine whether a livestock animal is present in the vicinity of the livestock treatment device 120. To do so, the livestock presence detection module 1502 may monitor the sensor data produced by the presence sensor 1322 and determine the presence (or lack thereof) of a livestock animal based on such sensor data. As discussed above, in some embodiments, the livestock presence detection module 1502 may determine the presence of a livestock animal based on transmission received from a livestock identification tag 130 coupled to the livestock animal.

The livestock identification determination module 1504 is configured to determine the identity of a livestock animal that has been detected within the vicinity of the livestock treatment device 120 by the livestock presence detection module 1502. To do so, the livestock identification determination module 1504 receives livestock identification data from the livestock identification tag 130 coupled to the detected livestock animal. In some embodiments, the livestock identification determination module 1504 may transmit, via the identification tag communication circuit 1326, an interrogation signal to the livestock identification tag 130 to cause the livestock identification tag 130 to transmit its corresponding livestock identification data.

The livestock treatment list management module 1506 is configured to receive, via the communication circuit 1324, a livestock treatment list 1510 from the livestock health monitoring server 102 and store the livestock treatment list 1510 in the memory 1314 (or other data storage of the livestock treatment device 120). As discussed above, the livestock treatment list includes the livestock identification data of each livestock animal to which the corresponding livestock treatment device 120 is to provide treatment.

The livestock treatment list management module 1506 is also configured to compare any livestock identification data received by the livestock identification determination module 1504 to the livestock treatment list to determine whether a particular livestock animal is to be provided treatment. If the livestock treatment list management module 1506 determines that a present livestock animal is to be treated based on such comparison, the actuator control module 1508 is configured to control the operation of the actuator 1320 to provide the treatment. For example, if the livestock treatment list management module 1506 determines that a livestock animal having livestock identification data included on the livestock treatment list is presently eating at a feeding station managed by the livestock treatment device 120, the actuator control module 1508 may activate the actuator 1320 to dispense a medicine to the livestock animal, reduce the amount of food provided to the livestock animal, and/or provide some other form of treatment.

Figure 16:
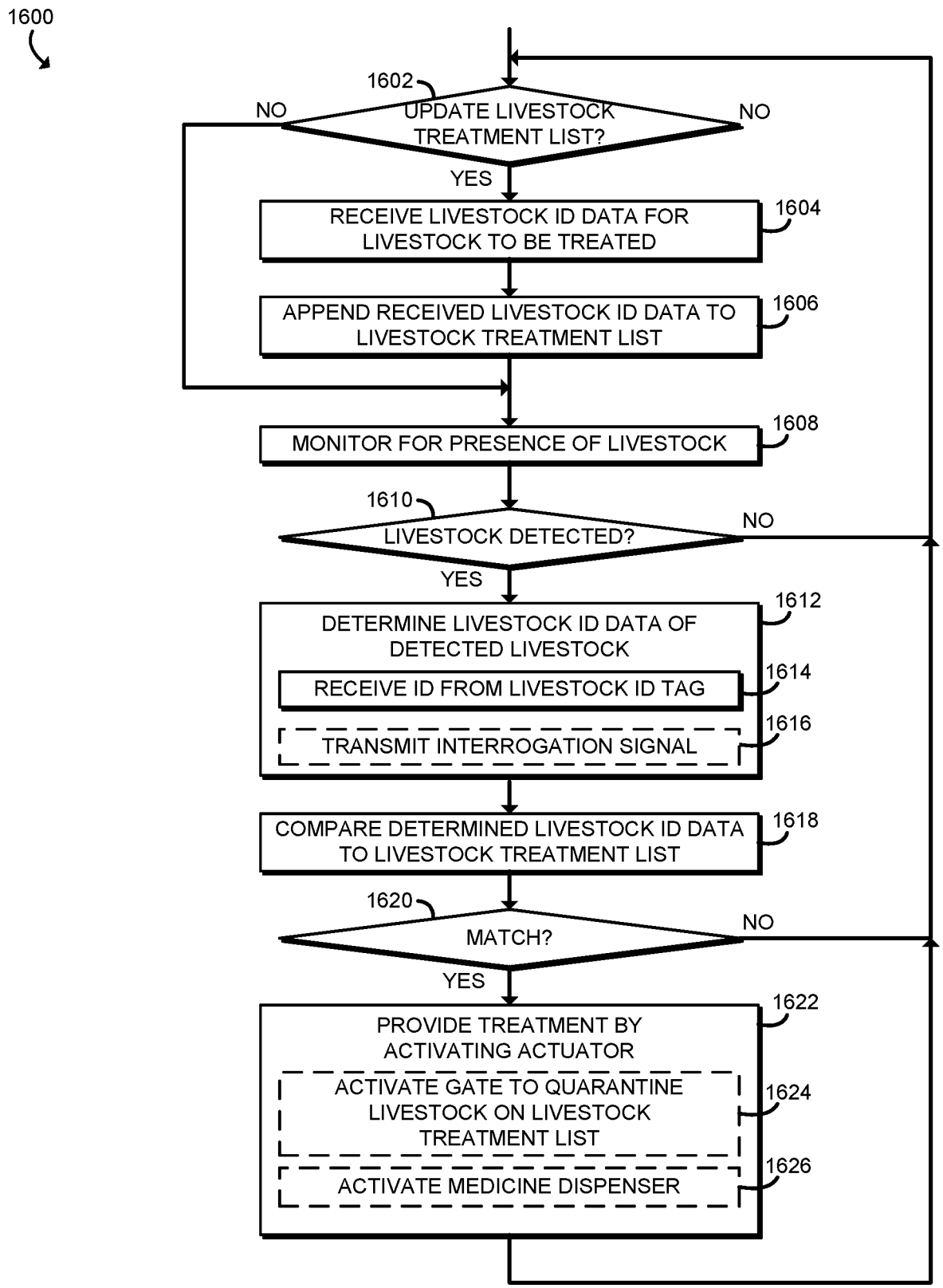
FIG. 16 is a simplified flow diagram of at least one embodiment of a method for providing treatment to a livestock animal that may be executed by the livestock treatment device of FIGS. 9 and 10.

Referring now to FIG. 16, in use, each livestock treatment device 120 may execute a method 1600 for providing treatment to a livestock animal. The method 1600 begins with block 1602 in which the livestock treatment device 120 determines whether an update to the livestock treatment list has been received from the livestock health monitoring server 102. For example, the livestock health monitoring server 102 may periodically update the livestock treatment list with additional livestock identification data identifying new livestock animals to be added to the livestock treatment list. Alternatively, the livestock health monitoring server 102 may update the livestock treatment device 120 by transmitting the complete livestock treatment list. Regardless, if the livestock treatment device 120 determines that an update to the livestock treatment list is available, the method 1600 advances to block 1604 in which the livestock treatment device 120 receives the livestock identification data identifying livestock animals to be treated from the livestock health monitoring server 102. In block 1606, the livestock treatment device 120 appends or adds the newly received livestock identification data to the livestock treatment list maintained by the livestock treatment device 120.

If not update to the livestock treatment list is available or after the livestock treatment list has been updated, the method 1600 advances to block 1608. In block 1608, the livestock treatment device 120 monitors for the presence of a livestock animal in the vicinity of the livestock treatment device 120. To do so, as discussed above, the livestock treatment device 120 may analyze the sensor data produced by the presence sensor 1322. In block 1610, the livestock treatment device 120 determines whether the presence of a livestock animal has been detected. If not, the method 1600 loops back to block 1602 to continue monitoring for updates to the livestock treatment list. If, however, the presence of a livestock animal is detected, the method 1600 advances to block 1612. In block 1612, the livestock treatment device 120 determines the livestock identification data of the detected livestock animal. As discussed above, the livestock identification data uniquely identifies the associated livestock animal from other livestock animals of the corresponding herd. Illustratively, the livestock treatment device 120 determines the livestock identification data of the detected livestock animal by receiving, in block 1614, the livestock identification data from the livestock identification tag 130 coupled to the livestock animal. In some embodiments, in block 1616, the livestock treatment device 120 may transmit an interrogation signal to the livestock identification tag 130 of the detected livestock animal to cause the livestock identification tag 130 to transmit the livestock identification data associated with the detected livestock animal.

After the livestock treatment device 120 has obtained or determined the livestock identification data of the livestock animal, the method 1600 advances to block 1618 in which the livestock treatment device 120 compares the livestock identification data determined in block 1612 to the livestock treatment list. That is, the livestock treatment device 120 determines whether the detected livestock animal is to be treated by comparing the livestock identification data of the detected livestock animal to livestock treatment list. If the livestock treatment device 120 determines a match between the determine livestock identification data and the livestock treatment list in block 1620, the method 1600 advances to block 1622 in which the livestock treatment device 120 provides a treatment to the detected livestock animal by activating the actuator 1320. For example, in block 1624, the livestock treatment device 120 may activate a gate actuator to quarantine the detected animal. Additionally or alternatively, the livestock treatment device 120 may activate a medicine dispenser in block 1626 to dispense an amount of medicine to the detected livestock animal.

Figure 18:
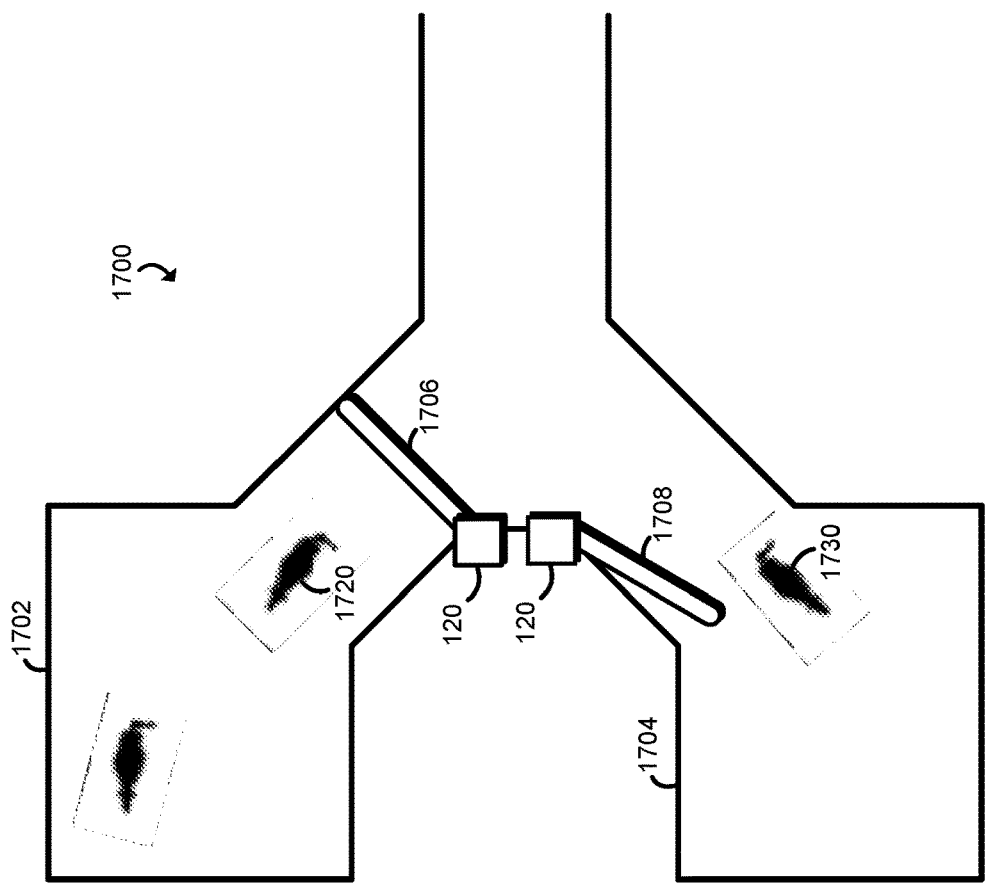
FIGS. 17 and 18 are simplified block diagrams of a sorting pen having a livestock treatment device controlling a sorting gate during operation of the method of FIG. 16.
Figure 17:
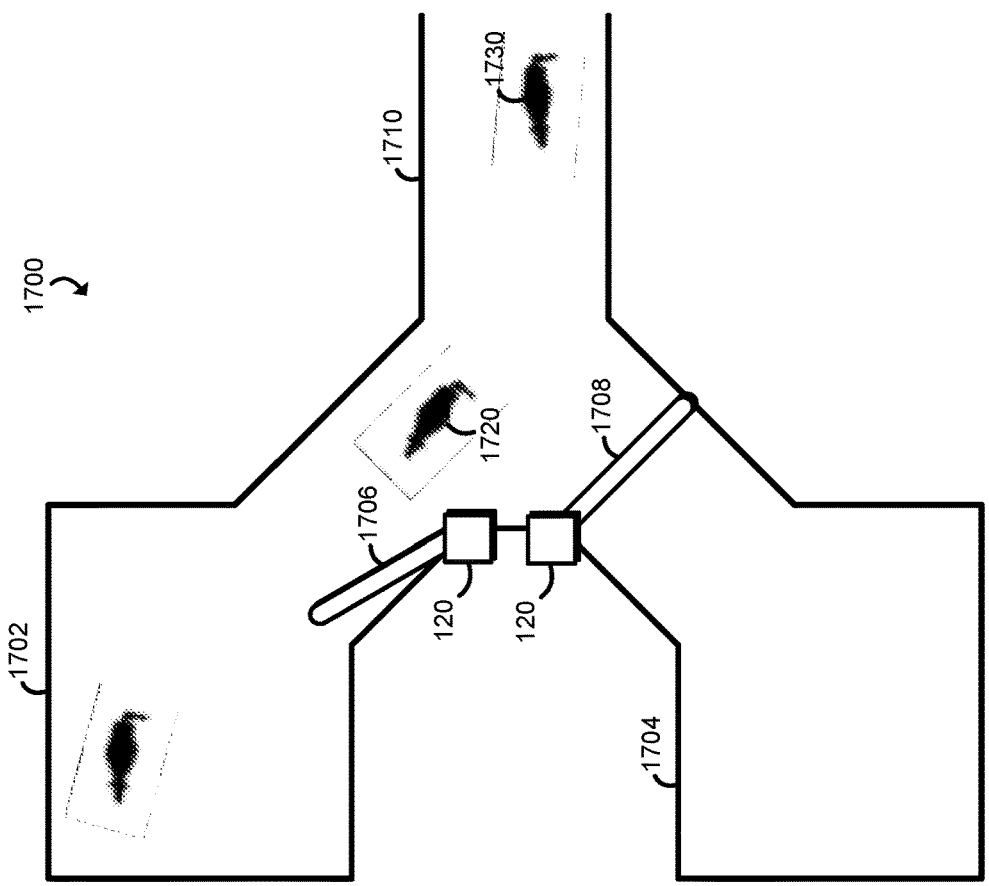

Referring now to FIGS. 17 and 18, an illustrative example of the system 100 applied to a sorting pen 1700 is shown. The sorting pen 1700 includes a roaming pen 1702 for healthy livestock animals and a quarantine pen 1704 of ill livestock animals or livestock animals under suspicion of being ill. A gate 1706 controls access to the roaming pen 1702, and a gate 1708 controls access to the quarantine pen 1704. As such, as livestock animals traverse down a corridor 1710 of the sorting pen 1700, the gates 1706, 1708 guide the livestock animals to the appropriate pen. To do so, the sorting pen 1700 includes a livestock treatment device 120 operatively coupled to each gate 1706, 1708. As a healthy livestock animal 1720 approaches the gates 1706, 1708, the livestock identification tag 130 of the healthy livestock animal 1720 transmits its livestock identification data to the livestock treatment devices 120. Each livestock treatment device 120 compares the livestock identification data to its respective treatment list, and the livestock treatment device 120 coupled to the gate 1706 actuates the gate 1706 to allow access of the healthy livestock animal 1720 into the roaming pen 1702 as shown in FIG. 17.

Subsequently, as an ill livestock animal 1730 approaches the gates 1706, 1708, the livestock identification tag 130 of the ill livestock animal 1730 transmits its livestock identification data to the livestock treatment devices 120. Each livestock treatment device 120 compares the livestock identification data to its respective treatment list, and the livestock treatment device 120 coupled to the gate 1708 actuates the gate 1708 to allow access of the ill livestock animal 1730 into the quarantine pen 1704 as shown in FIG. 18. In this way, the livestock treatment devices 120 are capable of applying treatment to livestock animals on a per-animal basis, rather than a per-herd basis.

Figure 19:
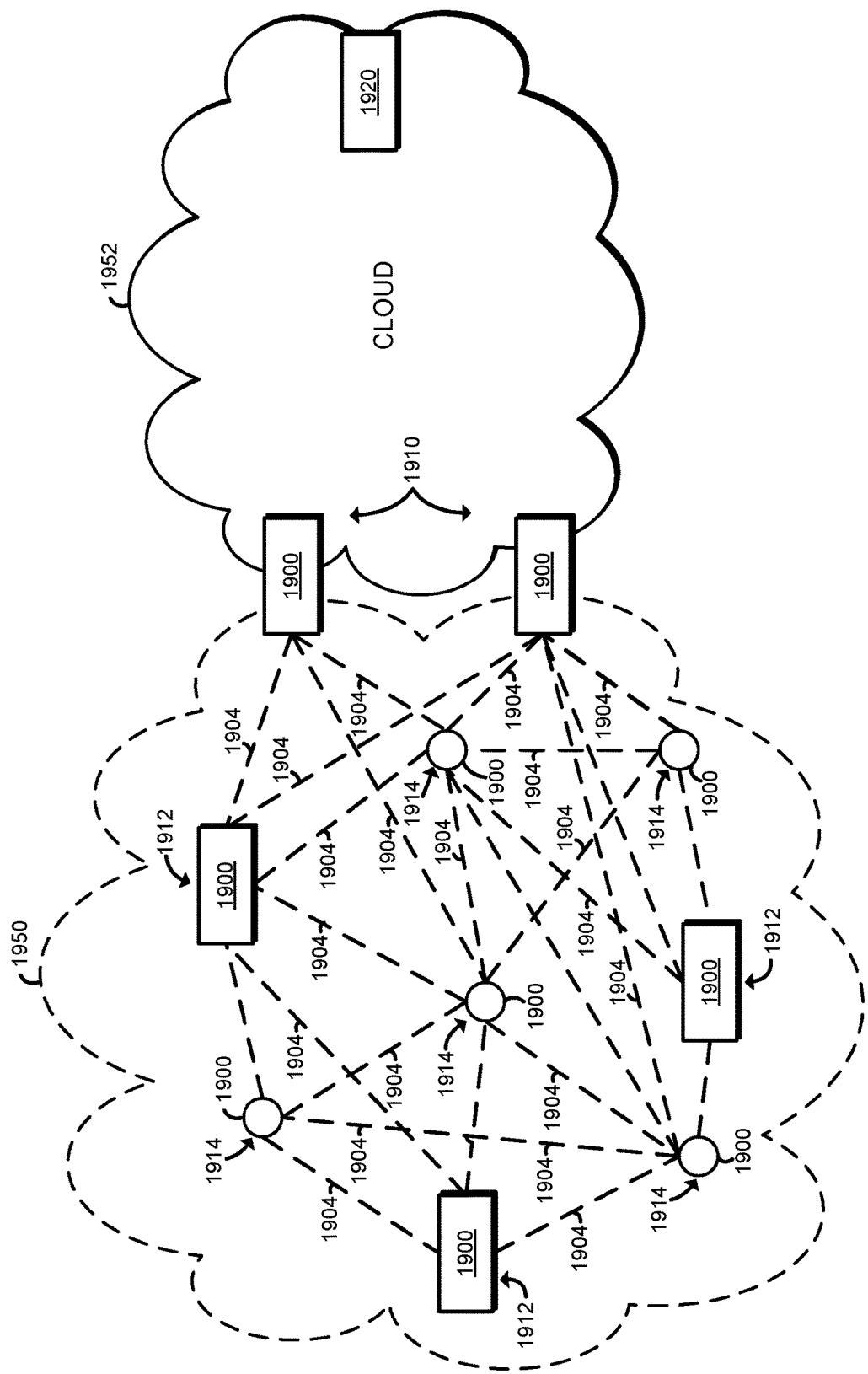
FIG. 19 is a simplified block diagram of another embodiment of the system of FIG. 1 having devices arranged in a mesh network.

Referring now to FIG. 19, in some embodiments, some or all of the livestock health sensor systems 110, the livestock treatment devices 120, and the livestock identification tags 130 may be embodied as Internet-of-Things devices 1900 and form, potentially with other devices, a mesh network, which may be termed as a fog 1950, operating at the edge of a cloud network 1952. The fog 1950 may be considered to be a massively interconnected network wherein a number of IoT devices 1900 are in communications with each other, for example, by radio links 1904 (all of which are not labeled in FIG. 19 to simplify the figure and for clarify). This may be performed using the open interconnect consortium (OIC) standard specification 1.0 released by the Open Connectivity Foundation™ (OCF) on Dec. 23, 2015. This standard allows devices to discover each other and establish communications for interconnects. Other interconnection protocols may also be used, including, for example, the optimized link state routing (OLSR) Protocol, or the better approach to mobile ad-hoc networking (B.A.T.M.A.N.), among others.

Three types of IoT devices 1900 are shown in the example embodiment of FIG. 19, gateways 1910, data aggregators 1912, and sensors 1914, although any combinations of IoT devices 1900 and functionality may be used. The gateways 1910 may be edge devices that provide communications between the cloud 1952 and the fog 1950, and may also provide the backend process function for data obtained from sensors 1914 (e.g., the livestock health sensor systems 110, etc.), such as the live health characteristic data (e.g., motion data, temperature data, weight data, blood analysis data, etc.), presence data indicative of the presence of a livestock animal, and/or other data. The data aggregators 1912 may collect data from any number of the sensors 1914, and perform the back end processing function for the analysis. The results, raw data, or both may be passed along to the cloud 1952 through the gateways 1910. The sensors 1914 may be full IoT devices 1900, for example, capable of both collecting data and processing the data. In some cases, the sensors 1914 may be more limited in functionality, for example, collecting the data and allowing the data aggregators 1912 or gateways 1910 to process the data.

Communications from any IoT device 1900 may be passed along the most convenient path between any of the IoT devices 1900 to reach the gateways 1910. In these networks, the number of interconnections provide substantial redundancy, allowing communications to be maintained, even with the loss of a number of IoT devices 1900. Further, the use of a mesh network may allow IoT devices 1900 that are very low power or located at a distance from infrastructure to be used, as the range to connect to another IoT device 1900 may be much less than the range to connect to the gateways 1910.

The fog 1950 of the IoT devices 1900 devices may be presented to devices in the cloud 1952, such as a server 1920 (which may be embodied as the livestock health monitoring server 102), as a single device located at the edge of the cloud 1952, e.g., a fog 1950 device. In this example, the alert notifications coming from the fog 1950 device may be sent without being identified as coming from a specific IoT device 1900 within the fog 1950. For example, an alert notification may indicate a sensed abnormal health data and include the associated livestock health characteristic data and livestock identification data, even though the specific IoT device 1900 that sensed the livestock health characteristic may not be specifically identified.

In some examples, the IoT devices 1900 may be configured using an imperative programming style, e.g., with each IoT device 1900 having a specific function and communication partners. However, the IoT devices 1900 forming the fog 1950 device may be configured in a declarative programming style, allowing the IoT devices 1900 to reconfigure their operations and communications, such as to determine needed resources in response to conditions, queries, and device failures. As an example, a query from a user located at a server 1920 about health data of a specific livestock animal may result in the fog 1950 selecting the IoT devices 1900, such as particular sensors 1914, needed to answer the query. The data from these sensors 1914 may then be aggregated and analyzed by any combination of the sensors 1914, data aggregators 1912, or gateways 1910, before being sent on by the fog 1950 device to the server 1920 to answer the query. In this example, IoT devices 1900 in the fog 1950 may select the sensors 1914 used based on the query, such as adding data from the feeding sensor system 210, the blood analysis sensor system 220, and the livestock gait sensor system 232 (see FIG. 2). Further, if some of the IoT devices 1900 are not operational, other IoT devices 1900 in the fog 1950 device may provide analogous data, if available (e.g., the livestock movement sensor system 230 may provide sensor data in place of a malfunctioning livestock gait sensor system 232).

EXAMPLES

Illustrative examples of the technologies disclosed herein are provided below. An embodiment of the technologies may include any one or more, and any combination of, the examples described below.

Example 1 includes a livestock health sensor system comprising a communication circuit to receive livestock identification data from a livestock identification tag coupled to a livestock animal, wherein the livestock identification data uniquely identifies the livestock animal from other livestock animals of a herd; a livestock health sensor to produce sensor data indicative of a health characteristic of the livestock animal; and a controller to (i) determine livestock health characteristic data indicative of the health characteristic of the livestock animal based on the sensor data, (ii) associate the livestock health characteristic data and the livestock identification data, and (iii) control the communication circuit to transmit the livestock characteristic data and the livestock identification data to a livestock health monitoring server.

Example 2 includes the subject matter of Example 1, and further including a presence sensor to generate presence sensor data indicative of a presence of the livestock animal relative to the livestock health sensor system, wherein the controller is further to determine whether the livestock animal is present relative to the livestock health sensor system based on the presence sensor data, and wherein to receive the livestock identification data comprises to receive, in response to detection of the presence of the livestock animal, the livestock identification data.

Example 3 includes the subject matter of any of Examples 1 and 2, and wherein the controller is further to control the communication circuit to transmit an interrogation signal to the livestock identification tag to cause the livestock identification tag to transmit the livestock identification data to the livestock health sensor system.

Example 4 includes the subject matter of any of Examples 1-3, and wherein to determine the livestock health characteristic data comprises to monitor the sensor data for a period of time and determine the livestock health characteristic data based on the monitored sensor data.

Example 5 includes the subject matter of any of Examples 1-4, and wherein the controller is further to analyze the livestock health characteristic data to determine whether an alert condition exists.

Example 6 includes the subject matter of any of Examples 1-5, and wherein to analyze the livestock health characteristic data comprises to compare the livestock health characteristic data to a threshold.

Example 7 includes the subject matter of any of Examples 1-6, and wherein the controller is further to control the communication circuit to transmit an alert notification to the livestock health monitoring server in response to a determination that the alert condition exists, wherein the alert notification provides an indication that the livestock health characteristic data is abnormal.

Example 8 includes the subject matter of any of Examples 1-7, and wherein the controller is further to control the communication circuit to transmit an alert notification to the livestock identification tag in response to a determination that the alert condition exists, wherein the alert notification provides an indication that the livestock health characteristic data is abnormal.

Example 9 includes the subject matter of any of Examples 1-8, and wherein the alert notification includes an instruction to cause the livestock identification tag to activate an indicator of the livestock identification tag.

Example 10 includes a livestock identification tag comprising a communication circuit; a memory having stored therein livestock identification data that uniquely identifies a livestock animal to which the livestock identification tag is to be coupled; and a controller communicatively coupled to the memory, wherein the controller is to retrieve the livestock identification tag from the memory and control the communication circuit to transmit the livestock identification tag to a compute device.

Example 11 includes the subject matter of Example 10, and wherein to retrieve the livestock identification data comprises to retrieve the livestock identification data from the memory in response to an interrogation signal received from the compute device.

Example 12 includes the subject matter of any of Examples 10 and 11, and wherein to transmit the livestock identification data comprises to broadcast the livestock identification data.

Example 13 includes the subject matter of any of Examples 10-12, and wherein to transmit the livestock identification data comprises to transmit the livestock identification data to a livestock health sensor system or a livestock treatment device.

Example 14 includes the subject matter of any of Examples 10-13, and wherein the communication circuit is further to receive an alert notification from the compute device.

Example 15 includes the subject matter of any of Examples 10-14, and wherein the alert notification includes livestock health characteristic data indicative of a health characteristic of the livestock animal, and wherein the controller is further to store the livestock health characteristic data in the memory.

Example 16 includes the subject matter of any of Examples 10-15, and further including an indicator to provide an indication, and wherein the alert notification comprises an instruction to activate the indicator of the livestock identification tag and the controller is further to active the indicator in response to the instruction.

Example 17 includes the subject matter of any of Examples 10-16, and wherein the indicator is a visual indicator.

Example 18 includes a livestock health monitoring server to manage livestock health data, the livestock health monitoring server comprising a communication module to receive, from a plurality of livestock health sensor systems, livestock health data related to a livestock animal, wherein the livestock health data comprises livestock health characteristic data indicative of a corresponding health characteristic of the livestock animal determined by a corresponding livestock health sensor system and an associated livestock identification data that uniquely identifies the livestock animal; a livestock health data management module to (i) aggregate the livestock health characteristic data with historical livestock health characteristic data of the livestock animal based on the livestock identification data to generate aggregated livestock health characteristic data and (ii) analyze the aggregated livestock health characteristic data to determine whether an alert condition exists; and an alert notification module to generate and transmit an alert notification in response to a determination that the alert condition exists.

Example 19 includes the subject matter of Example 18, and wherein to aggregate the livestock health data comprises to store the livestock health data in a memory of the livestock health monitoring server based on the livestock identification data associated with the livestock health characteristic data.

Example 20 includes the subject matter of any of Examples 18 and 19, and wherein to analyze the aggregated livestock health characteristic data comprises to analyze a historical trend of the aggregated livestock health characteristic data.

Example 21 includes the subject matter of any of Examples 18-20, and wherein the alert notification provides an indication that the aggregated livestock health characteristic data is abnormal.

Example 22 includes the subject matter of any of Examples 18-21, and wherein to transmit the alert notification comprises to transmit an alert notification to a livestock health sensor system, wherein the alert notification includes the livestock identification data.

Example 23 includes the subject matter of any of Examples 18-22, and wherein to transmit the alert notification comprises to transmit an alert notification to a livestock identification tag coupled to the livestock animal, wherein the alert notification includes an instruction to activate an indicator of the livestock identification tag.

Example 24 includes the subject matter of any of Examples 18-23, and wherein to transmit the alert notification comprises to transmit an alert notification to a livestock treatment device, wherein the alert notification includes the livestock identification data.

Example 25 includes the subject matter of any of Examples 18-24, and wherein the alert notification further includes an instruction to active an actuator of the livestock treatment device based on the livestock identification data.

Example 26 includes the subject matter of any of Examples 18-25, and wherein the livestock health data management module is further to analyze the livestock health characteristic data to determine whether another alert condition exists, and the alert notification module is further to transmit another alert notification in response to a determination that the another alert condition exists.

Example 27 includes the subject matter of any of Examples 18-26, and wherein to analyze the livestock health characteristic data comprises to compare the livestock health characteristic data to a reference threshold.

Example 28 includes the subject matter of any of Examples 18-27, and further including a memory having stored therein a livestock treatment list that identifies livestock identification data of livestock animals that are to be treated; wherein the livestock health data management module is further to add the livestock identification data to the livestock treatment list, and wherein to transmit the alert notification comprises to transmit the livestock treatment list to a livestock treatment device and wherein the alert notification includes an instruction to activate an actuator of the livestock treatment device based on the livestock treatment list data.

Example 29 includes a livestock treatment device to provide treatment to a livestock animal, the livestock treatment device comprising an actuator controllable to provide a treatment to the livestock animal; a communication circuit to receive livestock identification data from a livestock identification tag coupled to the livestock animal, wherein the livestock identification data uniquely identifies the livestock animal from other livestock animals of a herd; and a controller to (i) determine whether the livestock animal is to be treated based on the livestock identification data and (ii) control the actuator to provide the treatment to the livestock animal in response to a determination that the livestock animal is to be treated.

Example 30 includes the subject matter of Example 29, and further including a presence sensor to generate presence sensor data indicative of a presence of the livestock animal relative to the livestock treatment device, wherein the controller is to determine whether the livestock animal is present relative to the livestock treatment device based on the presence sensor data, and wherein to receive the livestock identification data comprises to receive the livestock identification data in response to a determination that the livestock animal is present.

Example 31 includes the subject matter of any of Examples 29 and 30, and wherein the controller is further to control the communication circuit to transmit an interrogation signal to the livestock identification tag to cause the livestock identification tag to transmit the livestock identification data to the livestock treatment device.

Example 32 includes the subject matter of any of Examples 29-31, and further including a memory having stored therein a livestock treatment list that identifies livestock identification data of livestock animals that are to be treated, and wherein to determine whether the livestock animal is to be treated comprises to compare the livestock identification data to the livestock treatment list.

Example 33 includes the subject matter of any of Examples 29-32, and wherein the communication circuit is further to receive update data from a livestock health monitoring server, wherein the update data comprises livestock identification data that identifies livestock animals to be treated, and the controller is further to update the livestock treatment list with the update data.

Example 34 includes the subject matter of any of Examples 29-33, and wherein the actuator comprises a gate actuator controllable to open a gate to allow passage through the gate by the livestock animal.

Example 35 includes the subject matter of any of Examples 29-34, and wherein the actuator comprises a medicine dispenser controllable to dispense a medicine to the livestock animal.

Example 36 includes a method for determining livestock health data of a livestock animal, the method comprising receiving, by a communication circuit of a livestock health sensor system, livestock identification data from a livestock identification tag coupled to a livestock animal, wherein the livestock identification data uniquely identifies the livestock animal from other livestock animals of a herd; determining, by a controller of the livestock health sensor system, livestock health characteristic data indicative of a health characteristic of the livestock animal based on sensor data produced by a livestock health sensor of the livestock health sensor system; associating, by the livestock health sensor system, the livestock health characteristic data and the livestock identification data; and transmitting, by a communication circuit of the livestock health sensor system, the livestock characteristic data and the livestock identification data to a livestock health monitoring server.

Example 37 includes the subject matter of Example 36, and further including generating, by a presence sensor of the livestock health sensor system, presence sensor data indicative of a presence of the livestock animal relative to the livestock health sensor system; and determining, by the controller, whether the livestock animal is present relative to the livestock health sensor system based on the presence sensor data, wherein receiving the livestock identification data comprises receiving the livestock identification data in response to a determination that the livestock animal is present.

Example 38 includes the subject matter of any of Examples 36 and 37, and wherein receiving the livestock identification data comprises transmitting, by the communication circuit, an interrogation signal to the livestock identification tag to cause the livestock identification tag to transmit the livestock identification data to the livestock health sensor system.

Example 39 includes the subject matter of any of Examples 36-38, and wherein determining the livestock health characteristic data comprises monitoring the sensor data generated by the livestock health sensor for a period of time and determining the livestock health characteristic data based on the monitored sensor data.

Example 40 includes the subject matter of any of Examples 36-39, and further including analyzing, by the controller, the livestock health characteristic data to determine whether an alert condition exists.

Example 41 includes the subject matter of any of Examples 36-40, and wherein analyzing the livestock health characteristic data comprises comparing the livestock health characteristic data to a threshold.

Example 42 includes the subject matter of any of Examples 36-41, and further including transmitting, by the communication circuit, an alert notification to the livestock health monitoring server in response to a determination that the alert condition exists, wherein the alert notification provides an indication that the livestock health characteristic data is abnormal.

Example 43 includes the subject matter of any of Examples 36-42, and further including transmitting, by the communication circuit, an alert notification to the livestock identification tag in response to a determination that the alert condition exists, wherein the alert notification provides an indication that the livestock health characteristic data is abnormal.

Example 44 includes the subject matter of any of Examples 36-43, and wherein the alert notification includes an instruction to cause the livestock identification tag to activate an indicator of the livestock identification tag.

Example 45 includes a method for providing an identity of a livestock animal, the method comprising retrieving, by a controller of a livestock identification tag coupled to the livestock animal, livestock identification data from a memory of the livestock identification tag, wherein the livestock identification data uniquely identifies the livestock animal; and transmitting, by a communication circuit of the livestock identification tag, the livestock identification data to a compute device.

Example 46 includes the subject matter of Example 45, and wherein retrieving the livestock identification data comprises retrieving the livestock identification data from the memory in response to an interrogation signal received from the compute device.

Example 47 includes the subject matter of any of Examples 45 and 46, and wherein transmitting the livestock identification data comprises broadcasting the livestock identification data.

Example 48 includes the subject matter of any of Examples 45-47, and wherein transmitting the livestock identification data comprises transmitting the livestock identification data to a livestock health sensor system or a livestock treatment device.

Example 49 includes the subject matter of any of Examples 45-48, and further including receiving, by the communication circuit, an alert notification from the compute device.

Example 50 includes the subject matter of any of Examples 45-49, and wherein the alert notification includes livestock health characteristic data indicative of a health characteristic of the livestock animal, and further comprising storing, by the controller, the livestock health characteristic data in the memory.

Example 51 includes the subject matter of any of Examples 45-50, and wherein the alert notification comprises an instruction to activate an indicator of the livestock identification tag, and further comprising activating, in response to the instruction, the indicator of the livestock identification tag.

Example 52 includes a method for managing livestock health data, the method comprising receiving, by a livestock health monitoring server and from a plurality of livestock health sensor systems, livestock health data related to a livestock animal, wherein the livestock health data comprises livestock health characteristic data indicative of a corresponding health characteristic of the livestock animal determined by a corresponding livestock health sensor system and an associated livestock identification data that uniquely identifies the livestock animal; aggregating, by the livestock health monitoring server, the livestock health characteristic data with historical livestock health characteristic data of the livestock animal based on the livestock identification data to generate aggregated livestock health characteristic data; analyzing, by the livestock health monitoring server, the aggregated livestock health characteristic data to determine whether an alert condition exists; and transmitting, by the livestock health monitoring server, an alert notification in response to a determination that the alert condition exists.

Example 53 includes the subject matter of Example 52, and wherein aggregating the livestock health data comprises storing the livestock health data in a memory of the livestock health monitoring server based on the livestock identification data associated with the livestock health characteristic data.

Example 54 includes the subject matter of any of Examples 52 and 53, and wherein analyzing the aggregated livestock health characteristic data comprises analyzing a historical trend of the aggregated livestock health characteristic data.

Example 55 includes the subject matter of any of Examples 52-54, and wherein the alert notification provides an indication that the aggregated livestock health characteristic data is abnormal.

Example 56 includes the subject matter of any of Examples 52-55, and wherein transmitting the alert notification comprises transmitting an alert notification to a livestock health sensor system, wherein the alert notification includes the livestock identification data.

Example 57 includes the subject matter of any of Examples 52-56, and wherein transmitting the alert notification comprises transmitting an alert notification to a livestock identification tag coupled to the livestock animal, wherein the alert notification includes an instruction to activate an indicator of the livestock identification tag.

Example 58 includes the subject matter of any of Examples 52-57, and wherein transmitting the alert notification comprises transmitting an alert notification to a livestock treatment device, wherein the alert notification includes the livestock identification data.

Example 59 includes the subject matter of any of Examples 52-58, and wherein the alert notification further includes an instruction to active an actuator of the livestock treatment device based on the livestock identification data.

Example 60 includes the subject matter of any of Examples 52-59, and further including analyzing, by the livestock health monitoring server, the livestock health characteristic data to determine whether another alert condition exists; and transmitting, by the livestock health monitoring server, another alert notification in response to a determination that the another alert condition exists.

Example 61 includes the subject matter of any of Examples 52-60, and wherein analyzing the livestock health characteristic data comprises comparing the livestock health characteristic data to a reference threshold.

Example 62 includes the subject matter of any of Examples 52-61, and further including adding, by the livestock health monitoring server, the livestock identification data to a livestock treatment list stored on the livestock health monitoring server, wherein the livestock treatment list identifies livestock identification data of livestock animals that are to be treated, and wherein transmitting the alert notification comprises transmitting the livestock treatment list to a livestock treatment device and wherein the alert notification includes an instruction to active an actuator of the livestock treatment device based on the livestock treatment list data.

Example 63 includes a method for providing a treatment to a livestock animal, the method comprising receiving, by a communication circuit of a livestock treatment device, livestock identification data from a livestock identification tag coupled to a livestock animal, wherein the livestock identification data uniquely identifies the livestock animal from other livestock animals of a herd; determining, by a controller of the livestock treatment device, whether the livestock animal is to be treated based on the livestock identification data; and actuating, by the controller, an actuator of the livestock treatment device to provide the treatment to the livestock animal in response to a determination that the livestock animal is to be treated.

Example 64 includes the subject matter of Example 63, and further including generating, by a presence sensor of the livestock treatment device, presence sensor data indicative of a presence of the livestock animal relative to the livestock treatment device; and determining, by the controller, whether the livestock animal is present relative to the livestock treatment device based on the presence sensor data, wherein receiving the livestock identification data comprises receiving the livestock identification data in response to a determination that the livestock animal is present.

Example 65 includes the subject matter of any of Examples 63 and 64, and wherein receiving the livestock identification data comprises transmitting, by the communication circuit, an interrogation signal to the livestock identification tag to cause the livestock identification tag to transmit the livestock identification data to the livestock treatment device.

Example 66 includes the subject matter of any of Examples 63-65, and wherein determining whether the livestock animal is to be treated comprises comparing the livestock identification data to a livestock treatment list stored in a memory of the livestock treatment device, wherein the livestock treatment list identifies livestock identification data of livestock animals that are to be treated.

Example 67 includes the subject matter of any of Examples 63-66, and further including receiving, by the communication circuit, update data from a livestock health monitoring server, wherein the update data comprises livestock identification data identifying livestock animals to be treated, and updating, by the controller, the livestock treatment list with the update data.

Example 68 includes the subject matter of any of Examples 63-67, and wherein actuating the actuator of the livestock treatment device comprises actuating a gate actuator to open a gate to allow passage through the gate by the livestock animal.

Example 69 includes the subject matter of any of Examples 63-68, and wherein actuating the actuator of the livestock treatment device comprises actuating a medicine dispenser to dispense a medicine to the livestock animal.

Example 70 includes one or more computer-readable storage media comprising a plurality of instructions that, when executed, cause a compute device to perform the method of any of Examples 36-69.

Example 71 includes a livestock health sensor system comprising means for receiving livestock identification data from a livestock identification tag coupled to a livestock animal, wherein the livestock identification data uniquely identifies the livestock animal from other livestock animals of a herd; means for determining livestock health characteristic data indicative of a health characteristic of the livestock animal based on sensor data produced by a livestock health sensor of the livestock health sensor system; means for associating the livestock health characteristic data and the livestock identification data; and means for transmitting the livestock characteristic data and the livestock identification data to a livestock health monitoring server.

Example 72 includes the subject matter of Example 71, and further including means for generating presence sensor data indicative of a presence of the livestock animal relative to the livestock health sensor system; and means for determining whether the livestock animal is present relative to the livestock health sensor system based on the presence sensor data, wherein the means for receiving the livestock identification data comprises means for receiving the livestock identification data in response to a determination that the livestock animal is present.

Example 73 includes the subject matter of any of Examples 71 and 72, and wherein the means for receiving the livestock identification data comprises means for transmitting an interrogation signal to the livestock identification tag to cause the livestock identification tag to transmit the livestock identification data to the livestock health sensor system.

Example 74 includes the subject matter of any of Examples 71-73, and wherein the means for determining the livestock health characteristic data comprises means for monitoring the sensor data generated by the livestock health sensor for a period of time and determining the livestock health characteristic data based on the monitored sensor data.

Example 75 includes the subject matter of any of Examples 71-74, and further including means for analyzing the livestock health characteristic data to determine whether an alert condition exists.

Example 76 includes the subject matter of any of Examples 71-75, and wherein the means for analyzing the livestock health characteristic data comprises means for comparing the livestock health characteristic data to a threshold.

Example 77 includes the subject matter of any of Examples 71-76, and further including means for transmitting an alert notification to the livestock health monitoring server in response to a determination that the alert condition exists, wherein the alert notification provides an indication that the livestock health characteristic data is abnormal.

Example 78 includes the subject matter of any of Examples 71-77, and further including means for transmitting an alert notification to the livestock identification tag in response to a determination that the alert condition exists, wherein the alert notification provides an indication that the livestock health characteristic data is abnormal.

Example 79 includes the subject matter of any of Examples 71-78, and wherein the alert notification includes an instruction to cause the livestock identification tag to activate an indicator of the livestock identification tag.

Example 80 includes a livestock identification tag comprising means for retrieving livestock identification data from a memory of the livestock identification tag, wherein the livestock identification data uniquely identifies the livestock animal; and means for transmitting the livestock identification data to a compute device.

Example 81 includes the subject matter of Example 80, and wherein the means for retrieving the livestock identification data comprises means for retrieving the livestock identification data from the memory in response to an interrogation signal received from the compute device.

Example 82 includes the subject matter of any of Examples 80 and 81, and wherein the means for transmitting the livestock identification data comprises means for broadcasting the livestock identification data.

Example 83 includes the subject matter of any of Examples 80-82, and wherein the means for transmitting the livestock identification data comprises means for transmitting the livestock identification data to a livestock health sensor system or a livestock treatment device.

Example 84 includes the subject matter of any of Examples 80-83, and further means for comprising receiving an alert notification from the compute device.

Example 85 includes the subject matter of any of Examples 80-84, and wherein the alert notification includes livestock health characteristic data indicative of a health characteristic of the livestock animal, and further comprising means for storing the livestock health characteristic data in the memory.

Example 86 includes the subject matter of any of Examples 80-85, and wherein the alert notification comprises an instruction to activate an indicator of the livestock identification tag, and further comprising means for activating the indicator of the livestock identification tag.

Example 87 includes a livestock health monitoring server comprising means for receiving, from a plurality of livestock health sensor systems, livestock health data related to a livestock animal, wherein the livestock health data comprises livestock health characteristic data indicative of a corresponding health characteristic of the livestock animal determined by a corresponding livestock health sensor system and an associated livestock identification data that uniquely identifies the livestock animal; means for aggregating the livestock health characteristic data with historical livestock health characteristic data of the livestock animal based on the livestock identification data to generate aggregated livestock health characteristic data; means for analyzing the aggregated livestock health characteristic data to determine whether an alert condition exists; and means for transmitting an alert notification in response to a determination that the alert condition exists.

Example 88 includes the subject matter of Example 87, and wherein the means for aggregating the livestock health data comprises means for storing the livestock health data in a memory of the livestock health monitoring server based on the livestock identification data associated with the livestock health characteristic data.

Example 89 includes the subject matter of any of Examples 87 and 88, and wherein the means for analyzing the aggregated livestock health characteristic data comprises means for analyzing a historical trend of the aggregated livestock health characteristic data.

Example 90 includes the subject matter of any of Examples 87-89, and wherein the alert notification provides an indication that the aggregated livestock health characteristic data is abnormal.

Example 91 includes the subject matter of any of Examples 87-90, and wherein the means for transmitting the alert notification comprises means for transmitting an alert notification to a livestock health sensor system, wherein the alert notification includes the livestock identification data.

Example 92 includes the subject matter of any of Examples 87-91, and wherein the means for transmitting the alert notification comprises means for transmitting an alert notification to a livestock identification tag coupled to the livestock animal, wherein the alert notification includes an instruction to activate an indicator of the livestock identification tag.

Example 93 includes the subject matter of any of Examples 87-92, and wherein the means for transmitting the alert notification comprises means for transmitting an alert notification to a livestock treatment device, wherein the alert notification includes the livestock identification data.

Example 94 includes the subject matter of any of Examples 87-93, and, wherein the alert notification further includes an instruction to active an actuator of the livestock treatment device based on the livestock identification data.

Example 95 includes the subject matter of any of Examples 87-94, and further including means for analyzing the livestock health characteristic data to determine whether another alert condition exists; and means for transmitting another alert notification in response to a determination that the another alert condition exists.

Example 96 includes the subject matter of any of Examples 87-95, and wherein the means for analyzing the livestock health characteristic data comprises means for comparing the livestock health characteristic data to a reference threshold.

Example 97 includes the subject matter of any of Examples 87-96, and further including means for adding the livestock identification data to a livestock treatment list stored on the livestock health monitoring server, wherein the livestock treatment list identifies livestock identification data of livestock animals that are to be treated, and wherein the means for transmitting the alert notification comprises means for transmitting the livestock treatment list to a livestock treatment device and wherein the alert notification includes an instruction to active an actuator of the livestock treatment device based on the livestock treatment list data.

Example 98 includes a livestock treatment device to provide treatment to a livestock animal, the livestock treatment device comprising means for receiving, livestock identification data from a livestock identification tag coupled to a livestock animal, wherein the livestock identification data uniquely identifies the livestock animal from other livestock animals of a herd; means for determining whether the livestock animal is to be treated based on the livestock identification data; and means for actuating an actuator of the livestock treatment device to provide the treatment to the livestock animal in response to a determination that the livestock animal is to be treated.

Example 99 includes the subject matter of Example 98, and further including means for generating presence sensor data indicative of a presence of the livestock animal relative to the livestock treatment device; and means for determining whether the livestock animal is present relative to the livestock treatment device based on the presence sensor data, wherein the means for receiving the livestock identification data comprises means for receiving the livestock identification data in response to a determination that the livestock animal is present.

Example 100 includes the subject matter of any of Examples 98 and 99, and wherein the means for receiving the livestock identification data comprises means for transmitting an interrogation signal to the livestock identification tag to cause the livestock identification tag to transmit the livestock identification data to the livestock treatment device.

Example 101 includes the subject matter of any of Examples 98-100, and wherein means for determining whether the livestock animal is to be treated comprises means for comparing the livestock identification data to a livestock treatment list stored in a memory of the livestock treatment device, wherein the livestock treatment list identifies livestock identification data of livestock animals that are to be treated.

Example 102 includes the subject matter of any of Examples 98-101, and further including means for receiving update data from a livestock health monitoring server, wherein the update data comprises livestock identification data identifying livestock animals to be treated, and means for updating the livestock treatment list with the update data.

Example 103 includes the subject matter of any of Examples 98-102, and wherein the means for actuating the actuator of the livestock treatment device comprises means for actuating a gate actuator to open a gate to allow passage through the gate by the livestock animal.

Example 104 includes the subject matter of any of Examples 98-103, and wherein means for actuating the actuator of the livestock treatment device comprises means for actuating a medicine dispenser to dispense a medicine to the livestock animal.

The invention claimed is:

1. A livestock health sensor system comprising:
   a presence sensor to generate presence sensor data indicative of a presence of a livestock animal relative to the livestock health sensor system;
   a communication circuit to receive livestock identification data from a livestock identification tag coupled to the livestock animal, wherein the livestock identification data uniquely identifies the livestock animal from other livestock animals of a herd;
   a livestock health sensor, computationally different from the presence sensor, to produce sensor data indicative of a physical health characteristic of the livestock animal, including a feeding proclivity of the livestock animal; and
   a controller to:
   (i) determine whether the livestock animal is present relative to the livestock health sensor system based on the presence sensor data,
   (ii) determine, in response to a determination that the livestock animal is present, livestock health characteristic data indicative of the health characteristic of the livestock animal based on the sensor data produced by the livestock health sensor,
   (iii) associate the livestock health characteristic data and the livestock identification data, and
   (iv) control the communication circuit to transmit the livestock characteristic data and the livestock identification data to a livestock health monitoring server.

2. The livestock health sensor system of claim 1, wherein to receive the livestock identification data the communication circuit is to receive, in response to detection of the presence of the livestock animal, the livestock identification data.

3. The livestock health sensor system of claim 1, wherein the controller is further to analyze the livestock health characteristic data to determine whether an alert condition exists.

4. The livestock health sensor system of claim 3, wherein the controller is further to control the communication circuit to transmit an alert notification to the livestock health monitoring server in response to a determination that the alert condition exists, wherein the alert notification provides an indication that the livestock health characteristic data is abnormal.

5. The livestock health sensor system of claim 1, wherein presence sensor and the livestock health sensor are located on a common compute platform and include different sensing logic.

6. A livestock identification tag comprising:
an indicator coupled to a housing of the livestock identification tag and configured to provide an indication;
a communication circuit to receive, from a compute device, an alert notification that includes an instruction to activate the indicator of the livestock identification tag, wherein the instruction includes an indication pattern and a length of activation time for the indicator;
a memory having stored therein livestock identification data that uniquely identifies a livestock animal to which the livestock identification tag is to be coupled; and
a controller communicatively coupled to the memory, wherein the controller is to (i) retrieve the livestock identification data from the memory and control the communication circuit to transmit the livestock identification data to the compute device, and (ii) activate the indicator in response to the instruction according to the indication pattern and the length of activation time.

7. The livestock identification tag of claim 6, wherein to retrieve the livestock identification data, the controller is to retrieve the livestock identification data from the memory in response to an interrogation signal received from the compute device.

8. The livestock identification tag of claim 6, wherein the communication circuit is further to receive, from the compute device, an alert notification that includes livestock health characteristic data indicative of a health characteristic of the livestock animal, and
wherein the controller is further to store the livestock health characteristic data in the memory.

9. A livestock treatment device to provide treatment to a livestock animal, the livestock treatment device comprising:
a food dispenser configured to dispense food to the livestock animal;
a medicine dispenser configured to dispense a medicine into the food dispensed by the food dispenser to the livestock animal, wherein the medicine dispenser includes an actuator controllable to dispense the medicine;
a communication circuit to receive livestock identification data from a livestock identification tag coupled to the livestock animal, wherein the livestock identification data uniquely identifies the livestock animal from other livestock animals of a herd; and
a controller to (i) determine whether the livestock animal is to be treated based on the livestock identification data and (ii) control the actuator to provide the medicine to the livestock animal and activate a gate to quarantine the livestock animal in response to a determination that the livestock animal is to be treated.

10. The livestock treatment device of claim 9, further including a presence sensor to generate presence sensor data indicative of a presence of the livestock animal relative to the livestock treatment device,
wherein the controller is to determine whether the livestock animal is present relative to the livestock treatment device based on the presence sensor data, and
wherein to receive the livestock identification data, the communication circuit is to receive the livestock identification data in response to a determination that the livestock animal is present.

11. The livestock treatment device of claim 9, further including a memory having stored therein a livestock treatment list that identifies livestock identification data of livestock animals that are to be treated, wherein to determine whether the livestock animal is to be treated, the controller is to compare the livestock identification data to the livestock treatment list.

12. The livestock treatment device of claim 11, wherein:
the communication circuit is further to receive update data from a livestock health monitoring server, wherein the update data includes livestock identification data that identifies livestock animals to be treated, and
the controller is further to update the livestock treatment list with the update data.

13. One or more non-transitory computer-readable storage media comprising a plurality of instructions that, when executed by a livestock health sensor system, cause the livestock health sensor system to:
determine whether the livestock animal is present relative to the livestock health sensor system based on presence sensor data generated by a presence sensor, wherein the presence sensor data is indicative of a presence of a livestock animal relative to the livestock health sensor system;
receive livestock identification data from a livestock identification tag coupled to a livestock animal, wherein the livestock identification data uniquely identifies the livestock animal from other livestock animals of a herd;
determine, in response to determining that the livestock animal in present, livestock health characteristic data indicative of a physical health characteristic of the livestock animal based on sensor data that includes a feeding proclivity of the livestock animal produced by a livestock health sensor of the livestock health sensor system, the livestock health sensor computationally different from the presence sensor;
associate the livestock health characteristic data and the livestock identification data; and
transmit the livestock characteristic data and the livestock identification data to a livestock health monitoring server.

14. The one or more non-transitory, computer-readable storage media of claim 13, wherein to receive the livestock identification data, the instructions cause the livestock health sensor system to receive the livestock identification data in response to a determination that the livestock animal is present.

15. The one or more non-transitory, computer-readable storage media of claim 13, wherein the plurality of instructions, when executed by the livestock health sensor system, further cause the livestock health sensor system to analyze the livestock health characteristic data to determine whether an alert condition exists.

16. The one or more non-transitory, computer-readable storage media of claim 15, wherein the plurality of instructions, when executed by the livestock health sensor system, further cause the livestock health sensor system to transmit an alert notification to the livestock health monitoring server in response to a determination that the alert condition exists, wherein the alert notification provides an indication that the livestock health characteristic data is abnormal.

17. One or more non-transitory, computer-readable storage media comprising a plurality of instructions that, when executed by a livestock identification tag, cause the livestock identification tag to:

retrieve a livestock identification data from a memory of the livestock identification tag, wherein the livestock identification data uniquely identifies the livestock animal;

transmit, by a communication circuit of the livestock identification tag, the livestock identification data to a compute device;

receive, from the compute device, an alert notification that includes an instruction to activate an indicator coupled to a housing of the livestock identification tag, wherein the instruction includes an indication pattern and a length of activation time for the indicator; and activate the indicator in response to the instruction according to the indication pattern and the length of activation time.

18. The one or more non-transitory, computer-readable storage media of claim 17, wherein the plurality of instructions, when executed by the livestock identification tag, further cause the livestock identification tag to:

receive, from the compute device, an alert notification that includes livestock health characteristic data indicative of a health characteristic of the livestock animal, and store the livestock health characteristic data in the memory.

19. One or more non-transitory, computer-readable storage media comprising a plurality of instructions that, when executed by a livestock treatment device, cause the livestock treatment device to:

receive livestock identification data from a livestock identification tag coupled to a livestock animal, wherein the livestock identification data uniquely identifies the livestock animal from other livestock animals of a herd;

determine whether the livestock animal is to be treated based on the livestock identification data;

activate a food dispenser to dispense food to the livestock animal; and actuate an actuator of a medicine dispenser of the livestock treatment device to dispense a medicine into the food dispensed by the food dispenser to provide the treatment to the livestock animal and activate a gate to quarantine the livestock animal in response to a determination that the livestock animal is to be treated.

20. The one or more non-transitory computer-readable storage media of claim 19, wherein the plurality of instructions, when executed by the livestock treatment device, further cause the livestock treatment device to:

generate presence sensor data indicative of a presence of the livestock animal relative to the livestock treatment device; and determine whether the livestock animal is present relative to the livestock treatment device based on the presence sensor data, wherein to receive the livestock identification data, the instructions cause the livestock treatment device to receive the livestock identification data in response to a determination that the livestock animal is present.

21. The one or more non-transitory, computer-readable storage media of claim 19, wherein to determine whether the livestock animal is to be treated, the instructions cause the livestock treatment device to compare the livestock identification data to a livestock treatment list stored in a memory of the livestock treatment device, wherein the livestock treatment list identifies livestock identification data of livestock animals that are to be treated.

22. The one or more non-transitory computer-readable storage media of claim 21, wherein the plurality of instructions, when executed by the livestock treatment device, further cause the livestock treatment device to:

receive update data from a livestock health monitoring server, wherein the update data includes livestock identification data identifying livestock animals to be treated, and update the livestock treatment list with the update data.

* * * * *